US010053686B2

(12) United States Patent
Kenrick et al.

(10) Patent No.: US 10,053,686 B2
(45) Date of Patent: Aug. 21, 2018

(54) METHODS FOR ONE STEP NUCLEIC ACID AMPLIFICATION OF NON-ELUTED SAMPLES

(71) Applicant: GE Healthcare UK Limited, Buckinghamshire (GB)

(72) Inventors: Michael Kenneth Kenrick, Cardiff (GB); Aidan Mark Emery, London (GB); Fiona Elizabeth Allan, London (GB); Bonnie Lee Webster, London (GB); Erik Leeming Kvam, Niskayuna, NY (US); Wei Gao, Niskayuna, NY (US)

(73) Assignee: GE HEALTHCARE UK LIMITED, Little Chalfont (GB)

( * ) Notice: Subject to any disclaimer, the term of this patent is extended or adjusted under 35 U.S.C. 154(b) by 145 days.

(21) Appl. No.: 14/774,259

(22) PCT Filed: Mar. 14, 2014

(86) PCT No.: PCT/US2014/027790
§ 371 (c)(1),
(2) Date: Sep. 10, 2015

(87) PCT Pub. No.: WO2014/143714
PCT Pub. Date: Sep. 18, 2014

(65) Prior Publication Data
US 2016/0017315 A1 Jan. 21, 2016

Related U.S. Application Data

(60) Provisional application No. 61/788,068, filed on Mar. 15, 2013.

(51) Int. Cl.
*C12Q 1/68* (2018.01)
*C12N 15/10* (2006.01)
*C12Q 1/6806* (2018.01)
*C12Q 1/6848* (2018.01)
*C07H 21/02* (2006.01)

(52) U.S. Cl.
CPC ....... *C12N 15/1006* (2013.01); *C12Q 1/6806* (2013.01); *C12Q 1/6848* (2013.01)

(58) Field of Classification Search
CPC ........ C12Q 2523/308; C12Q 2527/125; C12Q 1/6806; C12Q 1/6848; C12N 15/1006
See application file for complete search history.

(56) References Cited

U.S. PATENT DOCUMENTS

| | | | | |
|---|---|---|---|---|
| 5,496,562 A * | 3/1996 | Burgoyne | .......... | C12N 15/1006 424/443 |
| 5,705,345 A * | 1/1998 | Lundin | .......... | C12Q 1/66 435/6.12 |
| 8,816,063 B2 | 8/2014 | Petzel et al. | | |
| 2002/0006615 A1 * | 1/2002 | Goldsborough | ... | C12N 15/1096 435/5 |
| 2004/0101895 A1 | 5/2004 | Fomovskaia et al. | | |
| 2010/0015621 A1 * | 1/2010 | Chang | .......... | C12Q 1/6806 435/6.18 |
| 2010/0173392 A1 * | 7/2010 | Davis | .......... | C12N 15/1006 435/280 |
| 2012/0156683 A1 * | 6/2012 | Baker | .......... | C12Q 1/6806 435/6.12 |
| 2015/0299770 A1 | 10/2015 | Tatnell et al. | | |

FOREIGN PATENT DOCUMENTS

| | | |
|---|---|---|
| WO | 99/38962 A2 | 8/1999 |
| WO | 2010/066908 A1 | 6/2010 |
| WO | 2012/128702 A1 | 9/2012 |
| WO | 2014/041093 A1 | 3/2014 |

OTHER PUBLICATIONS

Milne, E. et al., Cancer Epidemiol. Biomarkers Prev., vol. 15, pp. 816-819 (2006).*
Chum, P. et al., ThermoScientific Application Note 0013511J01U, pp. 1-3 (2011).*
GE Healthcare Life Sciences Data File 28-9844-02 AA, pp. 1-3 (2011).*
Yan Li et al. "An Optimized Method for Elution of Enteroviral RNA from a Cellulose-based Substrate," Journal of Virological Methods, vol. 186, No. 1-2, Dec. 1, 2012, pp. 62-67.
P. Gonzalez et al., "Evaluation of the FTA Carrier Device for Human Papillomavirus Testing in Developing Countries," Journal of Clinical Microbiology, vol. 50, No. 12, Sep. 19, 2012, pp. 3870-3876.
Carla R. Santos et al., "Use of FTA elute card impregnated with cervicovaginal sample directly into the amplification reaction increases the detection of human papillomavirus DNA," Brazillian Journal of Microbiology, vol. 43, No. 1, Jan. 1, 2012, pp. 389-392.
Pak Yang Chum et al. "Direct PCR from blood preserved on Whatman FTA and 903 Cards using Phusion Blood Direct PCT Kit," Dec. 1, 2008, pp. 1-1, retrieved from Internet: http://thermofisher.com.au/Uploads/file/Scientific/Applications/Life-Science-Research-Technologies/Direct-PCR-from-blood-preserved-on-Whatrnan-FTA-and-903-Cards.pdf, retrieved on Mar. 21, 2013, whole document.
Michaud et al. "Long-term storage at tropical temperature of dried-blood filter papers for detection and genotyping of RNA and DNA viruses by direct PCR," Journal of Virological Methods, Elsevier BV, NL, vol. 146, No. 1-2, Nov. 3, 2007, pp. 257-265.
Brian J. Taylor et al. "Real-time PCR detection of Plasmodium directly from whole blood and filter paper samples," Malaria Journal, Biomed Central, London GB, vol. 10, No. 1, Aug. 19, 2011, p. 244.

(Continued)

*Primary Examiner* — Teresa E Strzelecka
(74) *Attorney, Agent, or Firm* — Eversheds Sutherland (US) LLP

(57) ABSTRACT

The present invention relates to methods and kits which can be used to amplify nucleic acids with the advantage of decreasing user time and possible contamination. For easy processing and amplification of nucleic acid samples, the samples are bound to a solid support and used directly, without purification, in a nucleic acid amplification reaction such as the polymerase chain reaction (PCR).

16 Claims, 11 Drawing Sheets

(56) References Cited

OTHER PUBLICATIONS

Carlstedt et al. "Release of DNA from surfactant complexes induced by 2-hydroxypropyl-beta-cyclodextrin," International Journal of Biological Macromolecules, Elsevier BV, NL, vol. 46, No. 2, Mar. 1, 2010, retrieved on Dec. 16, 2009.

International Search Report and Written Opinion regarding International Application No. PCT/US2014/027790, dated Oct. 14, 2014, 16 pages.

Japanese Office Action for JP Application No. JP2016-502626 dated Mar. 23, 2018 (5 pages).

Abdelwhab et al., "The Use of FTA Filter Papres for Diagnosis of Avian Influenza Virus," Journal of Virological Methods, 2011, 174:120-122.

Kawasaki, "Amplification of RNA," PCR Protocols, A Guide to Methods and Applications, 1990, Chapter 3, pp. 21-27.

\* cited by examiner

SEQUENCE LISTING

<160> NUMBER OF SEQ ID NOS: 2

<210> SEQ ID NO 1
<211> LENGTH: 22
<212> TYPE: RNA
<213> ORGANISM: Artificial sequence
<220> FEATURE:
<223> OTHER INFORMATION: Synthetic oligonucleotide

<400> SEQUENCE: 1
uagcuuauca gacugauguu ga                                              22

<210> SEQ ID NO 2
<211> LENGTH: 22
<212> TYPE: RNA
<213> ORGANISM: Artificial sequence
<220> FEATURE:
<223> OTHER INFORMATION: synthetic oligonucleotide

<400> SEQUENCE: 2
ugagguagua guuugugcug uu                                              22

METHODS FOR ONE STEP NUCLEIC ACID AMPLIFICATION OF NON-ELUTED SAMPLES

This application is a filing under 35 U.S.C. 371 of international application number PCT/US2014/027790, filed Mar. 14, 2014, which claims priority to U.S. application No. 61/788,068, filed Mar. 15, 2013, the entire disclosures of each of which are hereby incorporated by reference.

This application claims priority to U.S. provisional patent application No. 61/788,068, filed Mar. 15, 2013, the disclosure of which is incorporated herein by reference in its entirety.

BACKGROUND OF THE INVENTION

Field of Invention

The present invention relates to the field of nucleic acid amplification, particularly to the use of a polymerase chain reaction to amplify nucleic acids. The invention provides methods and kits which can be used to amplify nucleic acids by combining a solid support such as an FTA™ paper with PCR reagents for one step amplification of nucleic acid samples. The invention has applications in the long term storage and easy processing of nucleic acids and is particularly useful in genotyping, diagnostics and forensics.

Background of the Invention

The polymerase chain reaction (PCR) is a common tool used in molecular biology for amplifying nucleic acids. U.S. Pat. No. 4,683,202 (Mullis, Cetus Corporation) describes a process for amplifying any desired specific nucleic acid sequence contained in a nucleic acid or mixture thereof.

Long-term storage, transport and archiving of nucleic acids on filter paper or chemically modified matrices is a well-known technique for preserving genetic material before the DNA or RNA is extracted and isolated in a form for use in genetic analysis such as PCR. Thus, EP 1563091 (Smith et al, Whatman) relates to methods for storing nucleic acids from samples such as cells or cell lysates. The nucleic acid is isolated and stored for extended periods of time, at room temperature and humidity, on a wide variety of filters and other types of solid support or solid phase media. Moreover, the document describes methods for storing nucleic acid-containing samples on a wide range of solid support matrices in tubes, columns, or multiwell plates.

WO 90/03959 (Burgoyne) describes a cellulose-based solid support for the storage of DNA, including blood DNA, comprising a solid matrix having a compound or composition which protects against degradation of DNA incorporated into or absorbed on the matrix. This document also discloses methods for storage of DNA using the solid medium, and for recovery of or in situ use of DNA.

U.S. Pat. No. 5,496,562 (Burgoyne) describes a cellulose-based solid medium and method for DNA storage. Method for storage and transport of DNA on the solid medium, as well as methods which involve either (a) the recovery of the DNA from the solid medium or (b) the use of the DNA in situ on the solid medium (for example, DNA sequence amplification by PCR) are disclosed. Unfortunately, the methods described only incorporates a surfactant or detergent on the surface of the solid medium and therefore suffer from the disadvantage that they require a separate step for the removal of the detergent before PCR is performed.

EP 2290099 B1 (Qiagen) describes again a method for processing and amplifying DNA. The method includes the steps of contacting the sample containing DNA to a solid support wherein a lysis reagent is bound to the solid support. The DNA is subsequently treated with a DNA purifying reagent and is purified. The application does not include a sequestrant on the solid support and requires a separate step for the removal of the lysis reagent and purification of the DNA before amplification.

WO 96/39813 (Burgoyne) describes a solid medium for storing a sample of genetic material and subsequent analysis; the solid medium comprising a protein denaturing agent and a chelating agent. The method described is for chelating agents which are any compound capable of complexing multivalent ions including Group II and Group III multivalent metal ions and transition metal ions. The invention does not specifically mention cyclodextrin as a chelating agent, nor does it suggest the PCR analysis could be performed in a single step.

U.S. Pat. No. 5,705,345 (Lundin et al.) describes a method of nucleic acid preparation whereby the sample containing cells is lysed to release nucleic acid and the sample is treated with cyclodextrin to neutralize the extractant. The advantage of this system is that conventional detergent removal requires a separation step however with the addition of cyclodextrin to neutralize the detergent it would remove the separation step needed and reduce chance of contamination.

GB 2346370 (Cambridge Molecular Technologies Ltd) describes applying a sample comprising cells containing nucleic acid to a filter, the cells are retained by the filter and contaminants are not. The cells are lysed on the filter and retained alongside the nucleic acid. Subsequent steps filter out the cell lysate while retaining the nucleic acid.

WO 96/18731 (Deggerdal) describes a method of isolating nucleic acid whereby the sample is bound to a solid support and sample is contacted with a detergent and subsequent steps performed to isolate the nucleic acid.

WO 00/53807 (Smith, Whatman) describes a medium for the storage and lysis of samples containing genetic material which can be eluted and analyzed. The medium is coated with a lysis reagent. In addition the medium could be coated with a weak base, a chelating agent, a surfactant and optionally uric acid.

WO 99/38962 (Health, Gentra Systems Inc.) describes a solid support with a bound lysis reagent. The lysis reagent can comprise of a detergent, a chelating agent, water and optionally an RNA digesting enzyme. The solid support does not contain cyclodextrin and requires further steps for purification of the nucleic acid for amplification analysis.

Current methods for DNA amplification involve a DNA purification procedure which often involves several steps which increases the chance of contamination. This is a tedious process and prior art methods have a number of clear disadvantages in terms of cost, complexity and in particular, user time. For example, column-based nucleic acid purification is a typical solid phase extraction method to purify nucleic acids. This method relies on the nucleic acid binding through adsorption to silica or other support depending on the pH and the salt content of the buffer. Examples of suitable buffers include Tris-EDTA (TE) buffer or Phosphate buffer (used in DNA microarray experiments due to the reactive amines). The purification of nucleic acids on such spin columns includes a number of complex and tedious steps. Nucleic acid purification on spin columns typically involves three time-consuming and complex steps/stages: the sample containing nucleic acid is added to the column and the nucleic acid binds due to the lower pH (relative to the silanol groups on the column) and salt concentration of the binding solution, which may contain buffer, a denaturing agent (such as guanidine hydrochloride), Triton X-100, isopropanol and a pH indicator;

the column is washed with 5 mM KPO4 pH 8.0 or similar, 80% EtOH); and the column is eluted with buffer or water.

Alternative methods involve the binding of nucleic acids in the presence of chaotropic salts such that DNA binds to silica or glass particles or glass beads. This property was used to purify nucleic acid using glass powder or silica beads under alkaline conditions. Typical chaotropic salts include guanidinium thiocyanate or guanidinium hydrochloride and recently glass beads have been substituted with glass containing minicolumns.

The best defense against PCR amplification failure in forensics applications is to combine sound sample handling and processing techniques with extraction systems proven to efficiently purify DNA.

Santos C. R. et al., (Brazilian Journal of Microbiology, 2012, 43, 389-392) describes a method of skipping the elution step prior to PCR amplification of nucleic acid and adding the punches directly into the PCR mix. The PCR amplification was performed for the detection of HPV-DNA and was more efficient than the standard FTA elute card protocol of eluting the nucleic acid prior to amplification. However this method only used qualitative PCR to measure the presence of HPV.

Nozawa N. et al., (Journal of Clinical Microbiology, 2007, 45, 1305-1307) describes a method of using real time PCR for the detection of cytomegalovirus (CMV). The method described involved the use of filter paper with purified CMV and was added directly to the PCR mix. The paper noted that only instruments with a photo-multiplier-tube scanning system could be used for real time PCR assays with filter disks. The paper suggests that the filter paper would adversely affect instruments using a charge-coupled device camera and therefore teaches away from the use of filter papers in real time PCR machines such as an ABI7700 machine.

Qiagen Sample & Assay Technologies Newsletter (March 2010, 15) describes the effects of a low $A_{260}/A_{230}$ ratio in RNA preparations on downstream PCR processing. The newsletter notes that increased absorbance at 230 nm in RNA samples is quite often due to contamination with guanidine thiocynate (a component of FTA elute cards and is used in RNA purification procedures). The experiments demonstrate $A_{260}/A_{230}$ ratio of an RNA sample is lower when guanidine thiocyanate is present, however guanidine thiocyanate concentrations up to 100 mM in an RNA sample did not affect the reliability of real-time PCR.

Typically the purification steps involved in the standard FTA elute card protocol can be cumbersome and purification can lead to a loss in DNA quality. There is therefore a need for an improved and simplified process for amplifying, quantifying and or profiling nucleic acid, which removes the need for a purification step. The present invention addresses this problem and provides methods and kits which can be used for single step amplification of nucleic acid from solid supports, particularly cellulose-derived supports.

SUMMARY OF INVENTION

The present invention provides methods and kits which can be used to amplify nucleic acids by contacting a solid support with nucleic acid and amplifying the nucleic acid in the presence of said solid support for easy amplification of DNA samples.

According to a first aspect of the present invention, there is provided a method for amplification of nucleic acid comprising the steps i) transferring, to a reaction vessel, a solid support comprising an impregnated chemistry contacted with a cellular sample containing a target nucleic acid;

ii) incubating said nucleic acid on the solid support with a high pH solution sufficient to elute the nucleic acid from said sample;

iii) amplifying the nucleic acid to produce amplified nucleic acid; and iv) quantifying the amplified nucleic acid.

In one embodiment, the method further includes using Short Tandem Repeat (STR) profiling to produce an STR profile.

In certain embodiments, the high pH solution is a solution having a pH of between about 10 to about 14. In a preferred embodiment, the high pH solution is a solution having a pH of between about 11 to about 13.5. In a more preferred embodiment, the high pH solution is a solution having a pH of between about 12 to about 13.

In another embodiment of the invention, the eluted and denatured nucleic acid is contained in a minimum volume (e.g., 5-200 microliters), below which the eluted chemistry and other cellular components causes an inhibition of subsequent analytical procedures.

In another embodiment of the invention, the method of the invention further comprises the addition of a neutralizing solution such that a minimum volume so formed permits downstream molecular biology applications.

In another embodiment of the invention, the eluted nucleic acid comprises a DNA or RNA species. In certain embodiments, the nucleic acid is amplified in the presence of an RNase inhibitor and alpha-cyclodextrin such that amplification occurs efficiently and without loss or inhibition In another embodiment of the invention, the eluted nucleic acid is mRNA, miRNA, rRNA, piRNA, or siRNA and the method further comprises gene expression analysis In yet another embodiment of the invention, the proposed method of amplification comprises reverse transcription polymerase chain reaction, isothermal amplification or quantitative polymerase chain reaction.

Still further, in a method of the invention the nucleic acid amplification reagent solution comprises a polymerase, deoxyribonucleotide triphosphate (dNTP), a reaction buffer and at least one primer, wherein the primer is optionally labelled with a dye.

In another embodiment, the composition of the solid support comprises guanidine thiocyanate, guanidine chloride, guanidine hydrochloride, sodium dodecyl sulphate, uric acid, EDTA or Tris buffer.

According to another embodiment of the invention, the solid support is washed with an aqueous solution before step i).

Still further, an embodiment of the invention comprises a solid support selected from the group consisting of a glass or silica-based solid phase medium, a plastics based solid phase medium, a cellulose-based solid phase medium, glass fiber, glass microfiber, silica gel, silica oxide, nitrocellulose, carboxymethylcellulose, polyester, polyamide, carbohydrate polymers, polypropylene, polytetraflurorethylene, polyvinylidenefluoride, wool and porous ceramics.

In another embodiment, the solid support is a cellulose based matrix.

In another embodiment, the cellulose based matrix is in the form of a pre punched disc.

A still further embodiment provides that the cellulose based matrix is in the form of an FTA™ or FTA™ Elute card.

In another embodiment, the nucleic acid is stored on the solid support prior to step i).

In one embodiment, the nucleic acid is stored on the solid support for at least 30 minute. The nucleic acid may be immobilised on the solid support for longer periods, for example, for at least 24 hours, for at least 7 days, for at least 30 days, for at least 90 days, for at least 180 days, for at least one year, and for at least 10 years. In this way the nucleic acid may be stored in a dried form which is suitable for subsequent analysis. Typically, samples are stored at temperatures from −200° C. to 40° C. In addition, stored samples may be optionally stored in dry or desiccated conditions or under inert atmospheres.

According to another aspect of the present invention, there is provided a method for amplification of nucleic acid comprising the steps:
i) contacting a solid support comprising a chaotropic salt with a cellular sample containing nucleic acid,
ii) transferring said solid support to a reaction vessel,
iii) incubating said nucleic acid on the solid support with a nucleic acid amplification reagent solution,
iv) amplifying the nucleic acid to produce amplified nucleic acid,
v) quantifying the amplified nucleic acid; and optionally,
vi) using Short Tandem Repeat (STR) profiling to produce an STR profile,
wherein steps i) to vi) are carried out in the presence of the solid support.

The advantage of amplifying the nucleic acid in the presence of the solid support is to reduce the number of steps required for nucleic acid amplification, thus saving operator time and facilitating operator usage. Another advantage is to avoid any loss of target nucleic acid, particularly when the amount of sample is low.

In one aspect of the present invention, the solid support is already in the reaction vessel prior to the addition of said cellular sample.

In another aspect, the method of amplification is a polymerase chain reaction.

In another aspect, the method of amplification comprises reverse transcription polymerase chain reaction, isothermal amplification or quantitative polymerase chain reaction.

In a further aspect, the nucleic acid amplification reagent solution comprises a polymerase, deoxyribonucleotide triphosphate (dNTP), a reaction buffer and at least one primer, wherein said primer is optionally labeled with a dye. Such dyes may include fluorescence dye FAM™ or CyDye DIGE Fluor™ from GE Healthcare. The nucleic acid amplification reagent solution can be present in a dried form, such as a Ready-to-Go™ (RTG) format. The advantage of dried or lyophilized formulations of the polymerase chain reaction reagents is that they can be easily solubilized by the addition of water, thus saving operator time and facilitating operator usage. To minimize operator error, the dried reagent mixture can be pre-dispensed into the reaction vessel, such as the well of a multi-well plate. Examples of such an RTG mixture include Illustra Ready-to-Go RT-PCR beads available from GE Healthcare.

In a further aspect, the nucleic acid is selected from the group consisting of DNA, RNA and oligonucleotide. The term "nucleic acid" is used herein synonymously with the term "nucleotides" and includes DNA, such as plasmid DNA and genomic DNA; RNA, such as mRNA, tRNA, sRNA and RNAi; and protein nucleic acid, PNA.

In one aspect, the chaotropic salt is a guanidine salt.

In another aspect, said guanidine salt is selected from the group consisting of guanidine thiocyanate, guanidine chloride and guanidine hydrochloride.

In one aspect, the chaotropic salt is sodium salt such as sodium iodide.

In another aspect, the solid support is washed with an aqueous solution following step i).

In one aspect, the solid support is selected from the group consisting of a glass or silica-based solid phase medium, a plastics-based solid phase medium, a cellulose-based solid phase medium, glass fiber, glass microfiber, silica gel, silica oxide, nitrocellulose, carboxymethylcellulose, polyester, polyamide, carbohydrate polymers, polypropylene, polytetraflurorethylene, polyvinylidinefluoride, wool and porous ceramics.

In a further aspect, said cellulose based matrix is in the form of a pre punched disc.

In another aspect, said cellulose based matrix is in the form of an FTA™ Elute card.

In another aspect, said cellulose based matrix is in the form of an indicating FTA™ Elute (iFTAe) Card wherein the dye indicates the presence of a biological sample.

In one aspect, the amplified nucleic acid is quantified using a PCR imaging system.

In one aspect the cellular sample is selected from a group consisting of eukaryotic or prokaryotic cell, virus, bacteria, plant and tissue culture cells.

In another aspect, said cellular sample is selected from the group consisting of blood, serum, semen, cerebral spinal fluid, synovial fluid, lymphatic fluid, saliva, buccal, cervical cell, vaginal cell, urine, faeces, hair, skin and muscle. The cellular sample may originate from a mammal, bird, fish or plant or a cell culture thereof. Preferably the cellular sample is mammalian in origin, most preferably human in origin. The sample containing the nucleic acid may be derived from any source. This includes, for example, physiological/pathological body fluids (e.g. secretions, excretions, exudates) or cell suspensions of humans and animals; physiological/pathological liquids or cell suspensions of plants; liquid products, extracts or suspensions of bacteria, fungi, plasmids, viruses, prions, etc.; liquid extracts or homogenates of human or animal body tissues (e.g., bone, liver, kidney, etc.); media from DNA or RNA synthesis, mixtures of chemically or biochemically synthesized DNA or RNA; and any other source in which DNA or RNA is or can be in a liquid medium.

In a further aspect, the method is for use as a tool selected from the group consisting of a molecular diagnostics tool, a human identification tool, a forensics tool, STR profiling tool and DNA profiling.

In another aspect, the nucleic acid is stored on the solid support prior to step ii).

In one aspect, the nucleic acid is stored on the solid support for at least 30 minute. The nucleic acid may be immobilised on the solid support for longer periods, for example, for at least 24 hours, for at least 7 days, for at least 30 days, for at least 90 days, for at least 180 days, for at least one year, and for at least 10 years. In this way the nucleic acid may be stored in a dried form which is suitable for subsequent analysis. Typically, samples are stored at temperatures from −200° C. to 40° C. In addition, stored samples may be optionally stored in dry or desiccated conditions or under inert atmospheres.

The method of the invention can be used either in single tube or a high-throughput 96-well format in combination with automated sample processing as described by Baron et al., (2011, Forensics Science International: Genetics Supplement Series, 93, e560-e561). This approach would involve a minimal number of steps and increase sample throughput. The risk of operator-induced error, such as cross-contamination is also reduced since this procedure requires fewer manipulations compared to protocols associated with currently used, more labor intensive kits (e.g. QIAmp DNA blood mini kit, Qiagen). The risk of sample mix-up is also reduced since the procedure requires few manipulations Importantly, the method is readily transferable to a multi-well format for high-throughput screening. The present invention can thus improve sample processing for carrying out PCR reactions to aid genetic interrogations. The invention can be conducted in a 96 well/high throughput format to facilitate sample handling and thus eliminate batch processing of samples.

In a further aspect, the reaction vessel is a well in a multi-well plate. Multi-well plates are available in a variety of formats, including 6, 12, 24, 96, 384 wells (e.g. Corning 384 well multi-well plate, Sigma Aldrich).

In one aspect, the sample is transferred to the reaction vessel by punching or cutting a disc from the solid support. Punching the portion or disc from the solid support can be effected by use of a punch, such as a Harris Micro Punch (Whatman Inc.; Sigma Aldrich)

According to another aspect of the present invention there is provided a method for amplification of nucleic acid comprising the steps:
i) contacting a solid support comprising a lysis reagent with a cellular sample containing nucleic acid,
ii) transferring said solid support to a reaction vessel,
iii) incubating said nucleic acid on the solid support with a nucleic acid amplification reagent solution,
iv) amplifying the nucleic acid to produce amplified nucleic acid, and
v) optionally, quantifying the amplified nucleic acid,
wherein steps i) to v) are carried out in the presence of the solid support.

In one aspect, the solid support is already in the reaction vessel prior to the addition of said cellular sample.

In another aspect, the method of amplification is a polymerase chain reaction.

In another aspect, the lysis reagent is selected from the group consisting of a surfactant, detergent and chaotropic salt.

In another aspect, the lysis reagent is selected from the group consisting of sodium dodecyl sulfate, guanidine thiocynate, guanidine chloride, guanidine hydrochloride and sodium iodide.

In a further aspect, the solid support is impregnated with sodium dodecyl sulfate (SDS), ethylenediaminetetracetic acid (EDTA) and uric acid.

In one aspect, the solid support is in the form of an FTA™ pre punched disc.

In another aspect, the cellulose based matrix is in the form of an indicating FTA™ (iFTA) Card wherein the dye indicates the presence of a biological sample.

In another aspect, the solid support is selected from the group consisting of a glass or silica-based solid phase medium, a plastics-based solid phase medium or a cellulose-based solid phase medium, glass fiber, glass microfiber, silica gel, silica oxide, nitrocellulose, carboxymethylcellulose, polyester, polyamide, carbohydrate polymers, polypropylene, polytetraflurorethylene, polyvinylidinefluoride, wool or porous ceramics.

In another aspect, the solid support is washed with an aqueous solution following step i).

In one aspect, the amplified nucleic acid is quantified using a PCR imaging system.

In one aspect, the cellular sample is selected from a group consisting of eukaryotic or prokaryotic cell, virus, bacteria, plant and tissue culture cells.

In another aspect, the cellular sample is selected from the group consisting of blood, serum, semen, cerebral spinal fluid, synovial fluid, lymphatic fluid, saliva, buccal, cervical and vaginal cells, urine, faeces, hair, skin and muscle. The cellular sample may originate from a mammal, bird, fish or plant or a cell culture thereof. Preferably the cellular sample is mammalian in origin, most preferably human in origin. The sample containing the nucleic acid may be derived from any source. This includes, for example, physiological/pathological body fluids (e.g. secretions, excretions, exudates) or cell suspensions of humans and animals; physiological/pathological liquids or cell suspensions of plants; liquid products, extracts or suspensions of bacteria, fungi, plasmids, viruses, prions, etc.; liquid extracts or homogenates of human or animal body tissues (e.g., bone, liver, kidney, etc.); media from DNA or RNA synthesis, mixtures of chemically or biochemically synthesized DNA or RNA; and any other source in which DNA or RNA is or can be in a liquid medium.

In a further aspect, the method is for use as a tool selected from the group consisting of a molecular diagnostics tool, a human identification tool, a forensics tool, STR profiling tool and DNA profiling.

In another aspect, the nucleic acid is stored on the solid support prior to step ii).

In one aspect, the nucleic acid is stored on the solid support for at least 30 minute. The nucleic acid may be immobilised on the solid support for longer periods, for example, for at least 24 hours, for at least 7 days, for at least 30 days, for at least 90 days, for at least 180 days, for at least one year, and for at least 10 years. In this way the nucleic acid may be stored in a dried form which is suitable for subsequent analysis. Typically, samples are stored at temperatures from −200° C. to 40° C. In addition, stored samples may be optionally stored in dry or desiccated conditions or under inert atmospheres.

The method of the invention can be used either in single tube or a high-throughput 96-well format in combination with automated sample processing as described by Baron et al., (2011, Forensics Science International: Genetics Supplement Series, 93, e560-e561). This approach would involve a minimal number of steps and increase sample throughput. The risk of operator-induced error, such as cross-contamination is also reduced since this procedure requires fewer manipulations compared to protocols associated with currently used, more labor intensive kits (e.g. QIAmp DNA blood mini kit, Qiagen). The risk of sample mix-up is also reduced since the procedure requires few manipulations Importantly, the method is readily transferable to a multi-well format for high-throughput screening. The present invention can thus improve sample processing for carrying out PCR reactions to aid genetic interrogations. The invention can be conducted in a 96 well/high throughput format to facilitate sample handling and thus eliminate batch processing of samples.

In a further aspect, the reaction vessel is a well in a multi-well plate. Multi-well plates are available in a variety of formats, including 6, 12, 24, 96, 384 wells (e.g. Corning 384 well multi-well plate, Sigma Aldrich).

In one aspect, the sample is transferred to the reaction vessel by punching or cutting a disc from the solid support. Punching the portion or disc from the solid support can be effected by use of a punch, such as a Harris Micro Punch (Whatman Inc.; Sigma Aldrich)

According to a third aspect of the present invention there is provided a kit for amplifying nucleic acid as herein before described and instructions for use thereof.

DETAILED DESCRIPTION OF THE INVENTION

Figure 1:
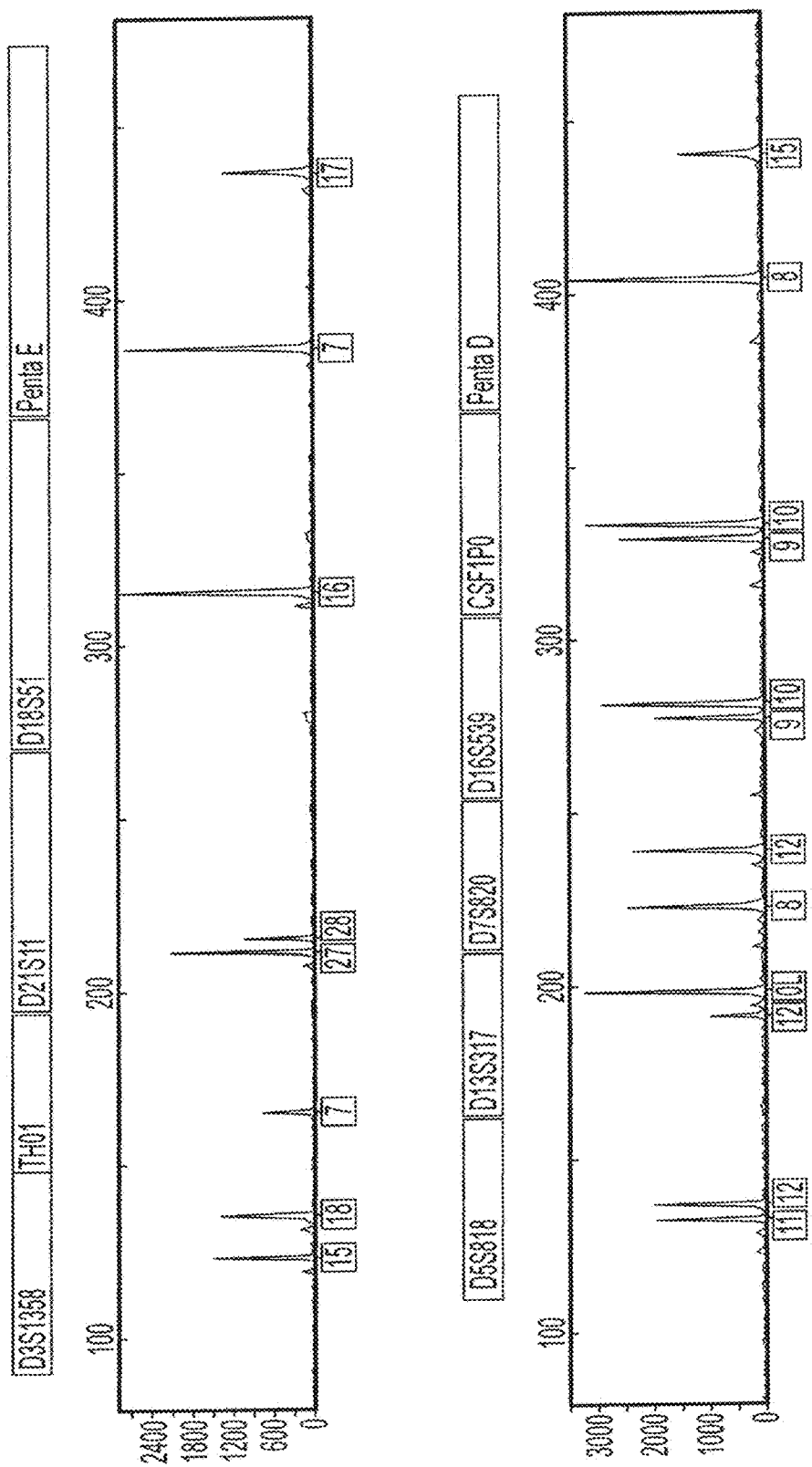
FIG. 1 presents the STR profile from the PCR amplification of unwashed HeLa cell spotted iFTAe (replicate no. 1).
Figure 1:
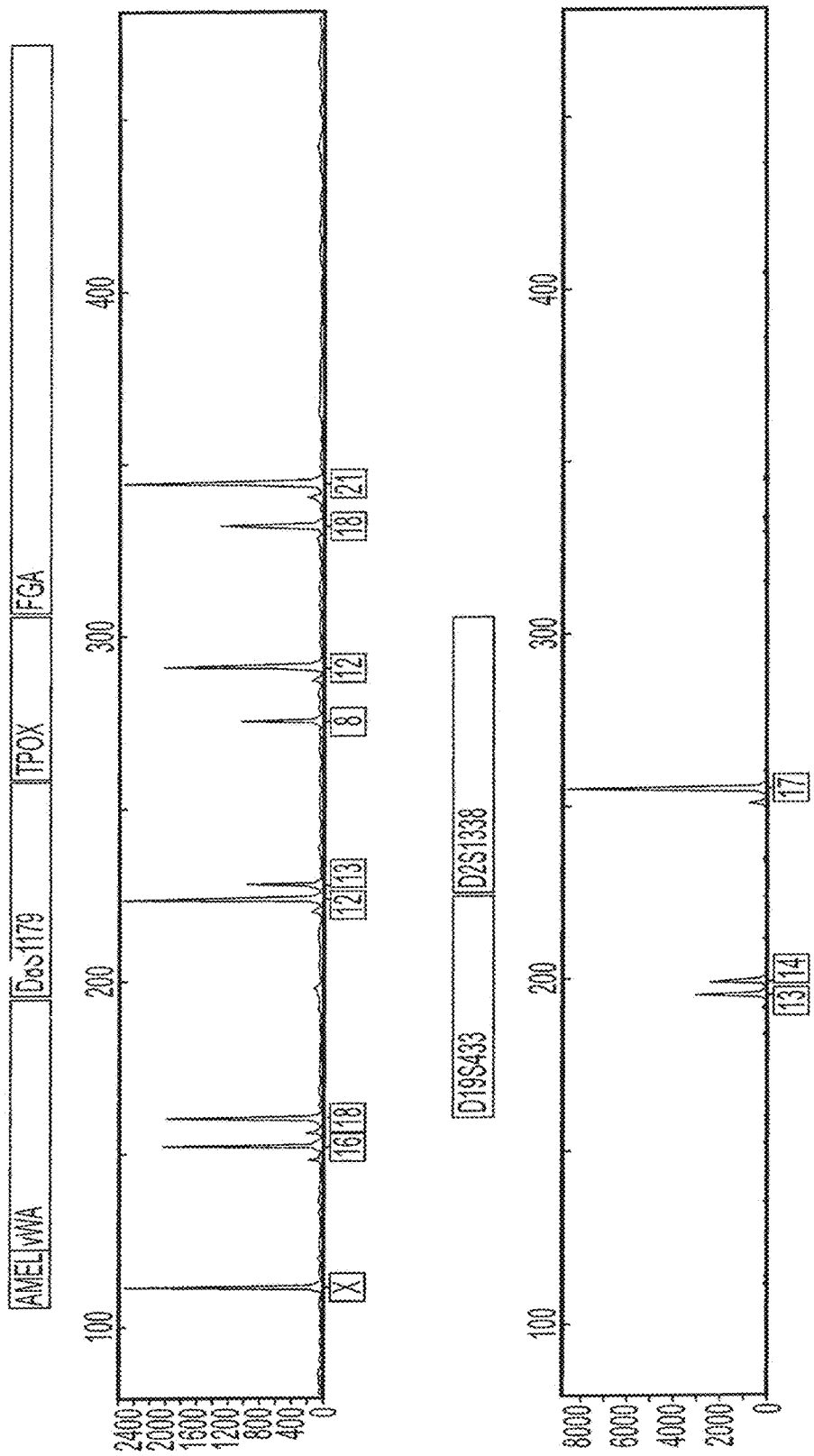

Potential use of the proposed methods of the invention includes but are not limited to those discussed infra.
(i) Forensic Workflow Automation:

Recent experimental results have shown that the non-wash optimized methodology, termed FTA Express, enables an efficient and loss-less/reduced-loss process in typical automated HID workflows. In general, the industry uses 1.2 mm FTA punches in either an Identifiler Direct or Powerplex 18D workflow where special amplification reaction mixtures and enzymes have been formulated to overcome the detergent chemistry contained in the non-washed FTA punch. The polymerase at this level of detergent would otherwise be denatured and render the STR reaction less efficient. The typical method is based on direct addition of one 1.2 mm punch into one tube or well containing a special STR formulation and having a total volume between 10-25 µl. In contrast, the invention proposes adding one 1.2 mm punch directly to a high pH elution buffer where a substantial amount of the DNA is rendered single stranded and diffuses rapidly into the general volume of the solution. Within a short time period of about 8-10 minutes a volume of neutralizing agent can be added to provide a combined total volume of 100-200 µl and containing approximately 0.05 to 0.2 ng/µl genomic DNA. This stock solution of DNA can then be used for multiple standard STR reactions (example disclose using Powerplex 16 HS) where multiples of 5-10 µl can be removed and added to parallel reactions. It is also possible to add a portion of the solution to qPCR reactions or general PCR reactions for amplification and adaption of amplicons for any molecular biology procedure. Of particular relevance is the ability enabled by the recent invention to establish an automated workflow that does not utilize 1.2 mm punches but perhaps uses 2 mm or 3 mm punches bearing significantly more DNA where the stoichiometric ratio of high pH elution buffer and neutralizer are used again with an approximate 10 minute processing time. This feature becomes important when it is recognized that the manipulation of 1.2 mm punches is challenging and special precautions need to be established to prevent misplacement of the punch on an automated system because of static discharge caused by consumable plastic ware. Because a facile system based on high volume elution has been developed as detailed herein, that is neither reliant on specially formulated PCR reagents or STR kits or on automated washing, it ensures that rapid workflows can be utilized in forensics and that punch loss because of static displacement of very small punches can be avoided. Further use of abrading sticks for scraping the surface of FTA punches and direct placement into high pH elution solution will likely enhance the miniaturization of the process that is not reliant on washing or on specially formulated amplification reactions.

Presently, there are many nucleic acid types that can be found in freshly spotted whole blood including small molecular weight nucleic acid species including microRNA, circulating nucleic acid (CNA), small viral genomes of various kinds and fragmented DNAs. However, conventional methods that teach or rely upon active washing and removal of denaturing chemistry are unsuitable to sustain such low molecular weight species on cellulose filters and other membranes. As a consequence, there is a constant threat that such washing steps may simply wash off such nucleic acid types thereby resulting in their loss before any detection strategies can be applied. A feature of the present invention aims to eliminate such loss.

A representative species of nucleic acid amenable to loss resulting from conventional methods that rely upon active washing and denaturing chemistry include CNAs. CNAs are a pool of low molecular weight nucleosome-derived DNAs that are typically less than 200 bp's and are described as being cell-free DNA. Circulating fetal-specific sequences have been detected and constitute a fraction of the total DNA in maternal plasma and can emanate from the unborn fetus. Because of this they are viewed by the scientific community as a "window on fetal genetics" and is different to amniocentesis that has some associated risk to the fetus. While this discovery may have piqued the interest of the researchers to develop noninvasive prenatal diagnostic approaches based simply on the analysis of a maternal blood sample, various technical challenges have impeded discovery of a standalone non-invasive diagnostic technique. For example, a big challenge has been the ability to discriminate fetal DNA from the coexisting background of maternal DNA in maternal plasma. During pregnancy, fetal DNA amounts to ≈3-6% of the total DNA in maternal plasma. These conditions require the processing and concentration of large sample volumes to achieve adequate amounts of fetal DNA for analysis. The high ratio of maternal to fetal DNA can further confound the downstream detection method when trying to interrogate copy number variations such as aneuploidy. This enrichment is highly significant when applied to detection methods and sequencing and could enable more accurate testing results earlier in the pregnancy than are currently available. Peter Brian Gahan, Circulating nucleic acids in plasma and serum: diagnosis and prognosis in cancer EPMA J. 2010 September; 1(3): 503-512.

The prior art also reveals that the diagnostic reliability of circulating DNA analysis depends on the fractional concentration of the targeted sequence, the analytical sensitivity, and the specificity. That the robust discrimination of single-nucleotide differences between circulating DNA species is technically challenging and demands the adoption of highly sensitive and specific analytical systems become very clear from a reading of the scientific literature. See for example, Anker, P., Mulcahy, H. & Stroun, M. (2003) Int. J. Cancer 103, 149-152. pmid:12455027, which discusses the biology and diagnostic applications of nucleic acids that are present in the plasma and serum of humans and Lo, Y. M. D., Chiu, R. W. K. & Johnson, P. J., eds. (2001) Circulating Nucleic Acids in Plasma or Serum II, Annals of the New York Academy of Sciences, Vol. 945 (N.Y. Acad. Sci., New York). That the reliable discrimination of subtle (e.g., single base) differences between fetal and maternal DNA in maternal plasma has hitherto been a technical challenge is also evident from Nasis, O., Thompson, S., Hong, T., Sherwood, M., Radcliffe, S., Jackson, L. & Otevrel, T. (2004) Clin. Chem. 50, 694-701). See also PNAS Jul. 20, 2004 vol. 101 no. 29 10762-10767.

The art is littered with various other examples demonstrating the development of noninvasive PCR based prenatal genetic tests for a variety of traits. However, a problem with such tests is that PCR based assays trade off sensitivity for specificity, making it difficult to identify particular mutations. Further, due to the stochastic nature of PCR, a population of molecules that is present in a small amount in the sample often is overlooked, such as fetal nucleic acid in a sample from a maternal tissue or body fluid. In fact, if rare nucleic acid is not amplified in the first few rounds of amplification, it becomes increasingly unlikely that the rare event will ever be detected. As well, there is also the potential that fetal nucleic acid in a maternal sample is degraded and not amendable to PCR amplification due to the small size of the nucleic acid. US Publication No. 2010/0216153.

Cell free nucleic acids have been proposed as biomarkers for various diseases exemplified by cancer, diabetes, Sickel Cell Disease, auto-immune diseases, myocardial infarction, Multiple Sclerosis etc. as and as well for particular physiological conditions such as intense physical exercise, hemodialysis, pregnancy. More, their presence or absence has also been linked to some clinical conditions such as trauma, sun burn, sepsis. Indeed, CNAs have been detected in many biological fluids, such as blood, urine, feces, milk, bronchial lavage and ascite. Refer to EP 2426217 A1.

Fetal aneuploidy (e.g., Down syndrome, Edward syndrome, and Patau syndrome) and other chromosomal aberrations affect 9 of 1,000 live births (Cunningham et al. in Williams Obstetrics, McGraw-Hill, New York, p. 942, 2002). Chromosomal abnormalities are generally diagnosed by karyotyping of fetal cells obtained by invasive procedures such as chorionic villus sampling or amniocentesis. Those procedures are associated with potentially significant risks to both the fetus and the mother. Noninvasive screening using maternal serum markers or ultrasound are available but have limited reliability (Fan et al., PNAS, 105 (42): 16266-16271, 2008). In the coming years, the detection of cell free nucleic acid, such as circulating nucleic acids e.g. DNA (cirDNA) or cirRNA, could become a non-invasive breakthrough technology that will allow the diagnosis of a specific pathological or physiological state, the prognosis and the follow-up of cancer, the choice of therapeutic orientation for each individual patient and the mass screening as a complement to the existing tests.

Researchers have suspected that necrotic and apoptotic processes during cancer cause cell-free DNA to be released from tumors and as a consequence any significant increase of CNA over and above the very low levels present in healthy individuals may signal the requirement for more in-depth diagnoses/intervention. Holdenrieder S, Burges A, Reich O, et al. DNA integrity in plasma and serum of patients with malignant and benign diseases. Ann NY Acad Sci. 2008; 1137:162-70. doi: 10.1196/annals.1448.013. Any washing procedures using conventional protocols applied to dried blood spots may lose these valuable biomarkers. Use of the inventive methods will help preserve these minute low molecular weight nucleosome derived DNA for further study. One possible instance when nucleosomes levels correlate with tumor stage and the presence of metastases is in gastrointestinal cancers. Umetani N, Kim J, Hiramats S, et al. Increased integrity of free circulating DNA in sera of patients with colorectal. Clin Chem. 2006; 52:1062-9. doi: 10.1373/clinchem.2006.068577.

More, circulating nucleosomes like CNAs are likely to find use in monitoring cytotoxic therapy wherein strongly decreasing levels are mainly found in patients with disease remission while constantly high or increasing values can be associated with progressive disease during chemo- and radiotherapy. Indeed, Holdenrieder supra reports that therapy outcome can be indicated by nucleosomal levels during the first week of chemo- and radiotherapy in patients with lung, pancreatic, and colorectal cancer as well as hematological malignancies.

Likewise, investigators have also observed an increase in the amount of free DNA in the blood that is correlated with cell death, as a function of tissue injury or inflammatory responses. Indeed, interrogating free DNA levels has been considered a telling prognostic indicator for numerous diseases including autoimmune disease, stroke, cancer and cardiovascular disease. However, the methodology to quantitatively assess free circulating DNA levels is expensive and time consuming and unreliable. Refer to US Patent Publication No. 2010/0216145.

(ii) microRNA

Rarely has a new research area gained such an overwhelming amount of attention as have microRNAs. Indeed, during the past two decades the field of eukaryotic gene regulation has changed dramatically due in part to the discovery of RNA-mediated gene silencing. A large part of gene regulation in eukaryotes takes place at the level of RNA-molecules. A group of endogenous regulatory RNA-molecules, the so-called microRNAs (miRNAs) appear to be involved in the regulation of about 30% of all human genes. These "small RNA" molecules (sRNA) also play a role in the development of diseases such as cancer, diabetes or neurological disorders.

microRNA's are a group of small regulatory RNA species that are typically 20-30 nt in length and have been implicated in health and disease including controlled cellular differentiation or uncontrolled cellular proliferation. They are generated in cells from miRNA precursors as a result of a series of RNA processing steps. microRNAs (miRNAs) have been shown to regulate gene expression through both translational attenuation and messenger RNA (mRNA) degradation. These small noncoding RNAs typically target multiple genes simultaneously, inducing subtle but reproducible shifts in target gene expression. Although several basic questions regarding their biological principles still remain to be answered, many specific characteristics of microRNAs in combination with compelling therapeutic efficacy data and a clear involvement in human disease have triggered the biotechnology community to start exploring the possibilities of viewing microRNAs as therapeutic entities.

Consequently, the study of small RNAs-RNA molecules on the order of 100 nucleotides or fewer-from various tissues in many organisms, as well as cultured cells, is an area of extreme interest now, and promises to remain one for the future. Brennecke, J. et al., PLOS Biol. 3(3): P85 (2005).

Disease-associated changes of miRNA expression patterns may provide new prognostic and diagnostic opportunities as well as potential clinical markers.

Usefulness of miRNA as therapeutic agents for treating various diseases are described in the art, e.g. WO 2009/126650 discloses the use of mi-126 and inhibitors of mi-126 for modulating angiogenesis. WO 2008/137867 ('867) describes compositions comprising miR-34 therapeutic agents for treating cancer. Cogswell J. P, et al., J. Alzheimers disease, 14, p 27-41, 2008, describes the identification of miRNA changes in Alzheimer's disease brain and CSF yields putative biomarkers and insights into disease pathways. WO 2008/137867 discloses that miRNA expression is altered in Alzheimer's CSF and that that changes for miRNA in CSF of normal and Alzheimer's disease can be detected.

Likewise, WO 2008/154333 details methods and compositions for identifying genes or genetic pathways modulated by miR-34, using miR-34 to modulate a gene or gene pathway, as well as of using this profile in assessing the condition of a patient and/or treating the patient with an appropriate miRNA.

Recently, microRNAs have been examined in plasma and serum for use in fetal diagnosis. See Chim SSC, Shing TKF, Hung ECW. Detection and characterization of placental microRNAs in maternal plasma. Clin Chem. 2008; 54:482-90. doi: 10.1373/clinchem.2007.09797; Hung ECW, Chiu RWK, Lo YMD. Detection of circulating fetal nucleic acids: a review of methods and applications. J Clin Path. 2009; 62:308-13. doi: 10.1136/jcp.2007.048470. MicroRNA's have also been implicated in a range of cancers. Lodes M J, Caraballo M, Suciu D, et al. Detection of cancer with serum microRNAs on an oligonucleotide microarray. PLoS ONE. 2009; 14:e622.

However, the key to the variously proposed studies relative to microRNA is the need to isolate RNA molecules in the size range of 15 to 100 nucleotides with high efficiency. As becomes clear from the discussion, infra, the current state of the art is innocently silent relative to an improved method for effectively isolating small quantities of mircoRNA for further study and exploitation.

Procedurally, the preparation of RNA from natural sources (tissue samples, whole organisms, cell cultures, bodily fluids) requires removal of all other biomolecules. Once water is eliminated, the primary component of cells is usually protein, often providing three-quarters of the mass. Of the major other biomolecules, lipids, carbohydrates, combinations of these with each other and protein, and DNA are the other main components. A goal of RNA extraction is to remove protein and DNA, as these provide the greatest interference in the use of RNA. Lipid and carbohydrate moieties can usually be dissolved away with the aid of a detergent. Protein can be stripped off RNA (and DNA) with the aid of detergents and denaturants, but still must be removed from the common solution. See US Patent Application, US 2005/0059024 ('024).

As noted in US 2005/0059024, at present, two main methods are used to accomplish this end. The first proposes the use of organic solvents that are immiscible with water to effectively dissolve or precipitate proteins, after which the aqueous, protein-free phase is separated by centrifugation prior to removal. Generally, phenol or phenol-chloroform mixtures are used for this purpose. The second method (solid-phase extraction) proposes selectively immobilizing the RNA on a solid surface and rinsing the protein away, followed by releasing the RNA in an aqueous solution. While, both procedures can reduce the amount of DNA contamination or carryover, its efficiency varies with the precise conditions employed.

While, phenol and phenol-chloroform extractions provide an extremely protein- and lipid-free solution of nucleic acid, much of the carbohydrate is also lost in this procedure. Likewise, acid phenol-chloroform is known to extract some of the DNA out of the aqueous solution. However, the solution is high in denaturing agents such as guanidinium hydrochloride, guanidinium thiocyanate, or urea, all of which are incompatible with downstream enzymatic analysis. RNA is usually separated from these mixtures by selective precipitation, usually with ethanol or isopropanol. Note, however, that use of this procedure is very ineffective for small nucleic acid molecules, such as, for example, small RNAs.

Solid-phase extraction on the other hand relies on high salt or salt and alcohol to decrease the affinity of RNA for water and increase it for the solid support used. The use of glass (silica) as a solid support has been demonstrated to work for large RNAs in the presence of high concentrations of denaturing salts—(U.S. Pat. Nos. 5,155,018; 5,990,302; 6,043,354; 6,110,363; 5,234,809) or lower concentrations of denaturing salts plus ethanol (U.S. Pat. No. 6,180,778). Importantly, normal conditions for binding to glass fiber or RNA do not work for microRNA, and the use of a raw lysate is problematic due to variable requirements with different tissues.

Consequently, many of the conventional protocols involve isolation of DNA or larger mRNA, which are not ideal for isolation of small RNA molecules because these are often not effectively captured and eluted. See US 2005/0059024.

Quantitative and qualitative isolation of miRNAs from various biological samples has been hampered for several reasons, including, but not limited to, labor-intensive and time consuming protocols; the nature of small size of miRNA invariably leads to easy loss of the targets during extraction; miRNAs, like other RNAs, are not stable and can be degraded easily during processing and storage; the miRNA detection rate from real patient samples is usually low or undetectable, i.e., not quantitative; and further the extracted miRNA targets normally are poorly correlated between related study objects.

As well, the prior art makes clear that in most cases miRNAs are present in a sample at low concentrations which are prone to be depleted during the purification steps or even getting lost. The art also makes clear that while it is possible to purify short RNAs from body fluids such as whole blood and also cell-free blood fractions (plasma or serum) by methods known in the prior art, this is done only with comparatively low yield. More, as noted in US 2012/0171675, the state of the current art lacks reliable methods useful in purifying free circulating nucleic acids such as, for example, microRNAs (miRNAs) from plasma or serum.

That there is a continuing need for improved methods for isolating and preserving small nucleic acid acids is evident from the following discussion that describes the challenges facing an investigator trying to isolate small quantities of microRNA http://www.invitrogen.com/site/us/en/home/References/Ambion-Tech-Support/microrna-studies/tech-notes/isolating-mima-for-profiling-studies.html. The discussion entails isolating miRNAs from samples of interest that include total RNA. The authors conclude that not all isolation methods retain the small RNA fraction, resulting in loss of miRNAs.

Technical hurdles in isolating minute amounts of mircoRNA from biological samples including the various drawbacks attended therewith is the subject matter of the following post http://www.genetics.pitt.edu/forms/flyers/miRNAextractionevaluation.pdf.

As regards commercially available isolation reagents or kits available from, for example, QIAGEN-PAXGENE blood RNA kit, AMBION-LEUKOLOCK etc. US 20120/208189 argues that such reagents/kits suffer from one or more of the following drawbacks: low sensitivity and detectability; low yield; not reproducible; large sample volume requirement; microRNA extraction does not scale well; low throughput.

To sum up, the standard washing practices described in all methods to date would efficiently remove important biomarkers such as CNAs and microRNAs and typically eliminate the use of FTA as a mean for microRNA analysis. An adaptation of the non-wash procedure described and claimed herein would effectively allow the target microRNA species to be preserved and not lost, which could subsequently be analyzed. An embodiment of the invention in accordance with this objective proposes applying an acidic elution followed by neutralization with high pH buffer to avoid damage caused to RNA species by exposing them first to high pH. As such, the methods of the invention would make it possible to isolate/purify very low concentrations of nucleic acids such as miRNAs.

(iii) Many types of viruses are known to infect humans and other species and can typically be found in the blood circulation. Many of these are low molecular weight nucleic acids and can be DNA or RNA in origin and can be circular or linear in nature. Because of their size it is likely that aggressive washing of FTA punches typically described in all published methods could result in the loss of significant numbers of genomic equivalents that would not allow viral copy number to be determined as a measure of health. This is especially important in chronic illnesses like HIV infection where the monitoring of viral copy number is essential for an effective drug therapy regime. Processes that use FTA or similar dried blood spot sampling should avoid washing at all costs to ensure that the viral copy number is preserved. Our new method is suitable for this analysis and would provide a simple approach compared to other methods.

(iv) Aged blood samples: It is known that aged blood samples applied to FTA are often of poor quality with respect to the molecular integrity of the total RNA and DNA in the sample. However modern methods have been developed like next generation sequencing that can exploit fragmented nucleic acid. The method(s) of the invention would further support these methodologies by helping preserve the molecular integrity of aged nucleic acids for use in next generation sequencing methodologies by limiting the loss of appreciable amounts of informative nucleic acid that would undoubtedly occur using current FTA procedures that call for aggressive washing steps.

What becomes clear from the above discussion is that current methods of isolating and preserving small nucleic acids such as CNA's, microRNAs, aged blood samples etc. were very unreliable and fraught with numerous drawbacks. Also, the widespread failure of others would not have motivated one to pursue a method as that described herein. If anything, such widespread failure of others would have necessarily dissuaded one skilled in the art away from pursuing further study in methods of isolating small nucleic acids especially in a competitive and cost conscious market place. Notwithstanding the above, presented herein is a novel method that effectively overcomes the drawbacks attendant with conventional workflows/methods and for the first time enables the isolation/purification of small nucleic acids which would allow for their preservation.

Experimental Results

Chemicals and Materials Used

A list of the chemicals and their sources is given below:
Indicating FTA™ elute micro (WB 120218 and WB 120411);
Indicating FTA™ elute cassette (WB 120230);
FTA Classic card (WB 120205)
Normal human blood (Tissue Solutions Ltd);
Genomic DNA (Promega product code G152A);
Harris Uni-core punch, 1.2 mm (Sigma, Catalogue number Z708860-25ea, lot 3110);
TaqMan Universal PCR master Mix, no AmpErase UNG (Applied Biosystems part number 4324018);
TaqMan RNase P Detection Reagents (Applied Biosystems part number 4316831)—contains RNase P primer;
Quantifiler qPCR kit, Applied Biosystems Part: 4343895
PowerPlex 18D (Promega code DC1802)—contains primers;
PowerPlex 16 HS (Promega Code: DC2101—contains primers;
Sterile water (Sigma Product code W4502);
Huma cervical epithelial cells (HeLa) (ATCC code CCL-2) and
Hi-Di Formamide (ABI code 4311320)

STR Profiles from Hela Cell Spotted Elute FTA Cards

Cultured HeLa cells at a concentration of $2.5\times10^6$ cell/ml were spotted onto an indicating FTA elute (iFTAe) card. A 1.2 mm punch was taken from the cell spotted FTA elute card and combined with a direct STR kit PowerPlex 18D reaction mix for a final volume of 25 µl. The 25 µl sample mix was added to each well of a 96 well PCR plate prior to amplification. Samples were analysed on a 3130×1 Capillary Electrophoresis using a 10 second sample injection.

PCR Reaction was Set Up as Follows:

Standards and samples were added to the appropriate wells. The plates were sealed and centrifuged at 1000 rpm for 1 minute. PCR was carried out on a Geneamp/ABI 9700 Thermo Cycler under the following thermal cycling conditions:

96° C. for 2 min, followed by 28 cycles of: 94° C. for 10 sec, 60° C. for 1 min, followed by 60° C. for 20 min, followed by a 4° C. Following amplification, visualization of PCR products was achieved using Capillary Electrophoresis. The results are presented graphically in FIGS. 1 to 4.

TABLE 1

Volume of reagents in HeLa cell reaction mix

| Ingredients | Volume |
| --- | --- |
| High Grade Water | 15 µl |
| Primers | 5 µl |
| Reaction mix | 5 µl |
| 1.2 mm punch of FTA elute containing HeLa cells. | 1 punch |

TABLE 2

Volume of reagents in DNA control reaction mix

| Ingredients | Volume |
| --- | --- |
| High Grade Water | 15 µl |
| Primers | 5 µl |

TABLE 2-continued

Volume of reagents in DNA control reaction mix

| Ingredients | Volume |
|---|---|
| Reaction mix | 5 μl |
| 2800M control DNA sample (5 ng/μl) | 1 μl |

TABLE 3

Volumes of reagents used in the Capillary Electrophoresis

| Ingredients | Volume |
|---|---|
| Hi-Di Formamide | 10 μl |
| CC5 Internal Lane Standard | 1 μl |
| PCR amplified cell sample or control DNA sample | 1 μl |
| Total volume | 12 μl |

FIG. 1 shows STR profile of unwashed HeLa cell spotted indicating FTA elute card combined with STR PCR reagents (replicate 1). The average peak height was 2313 RFU.

Figure 2:
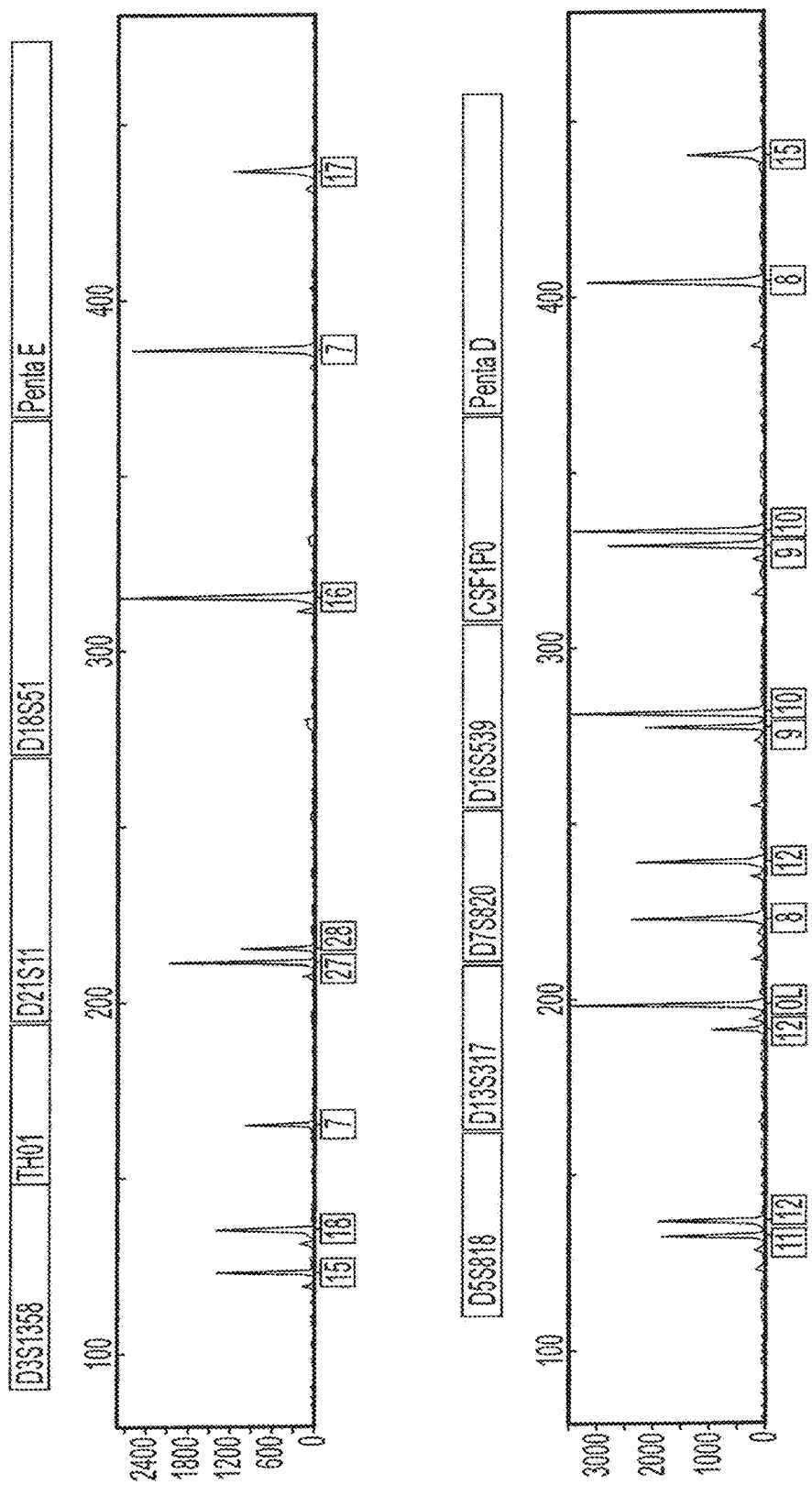
FIG. 2 presents the STR profile from the PCR amplification of unwashed HeLa cell spotted iFTAe (replicate no. 2).
Figure 2:
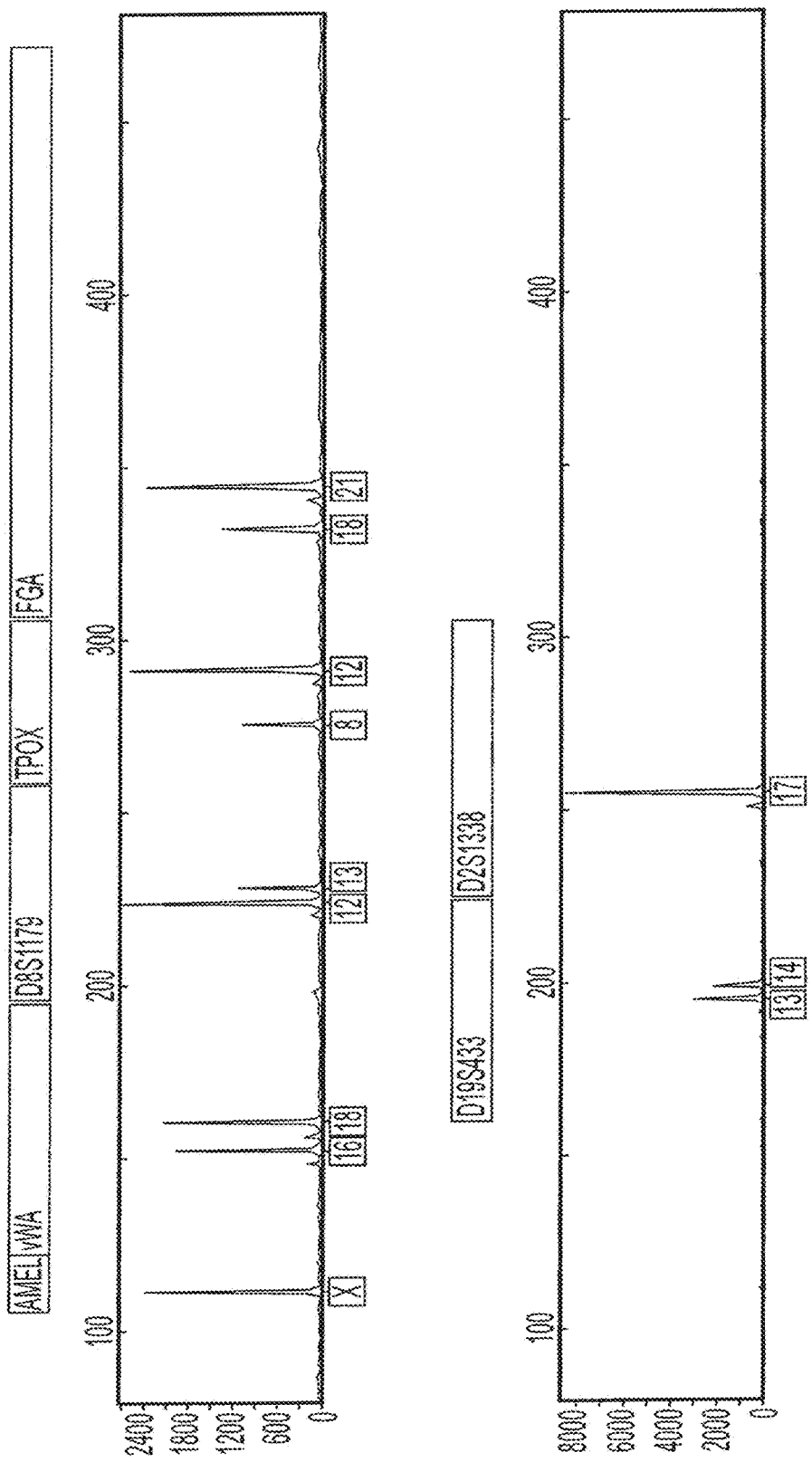

FIG. 2 shows STR profile of unwashed HeLa cell spotted indicating FTA elute card combined with STR PCR reagents (replicate 2). The average peak height was 2260 RFU.

Figure 3:
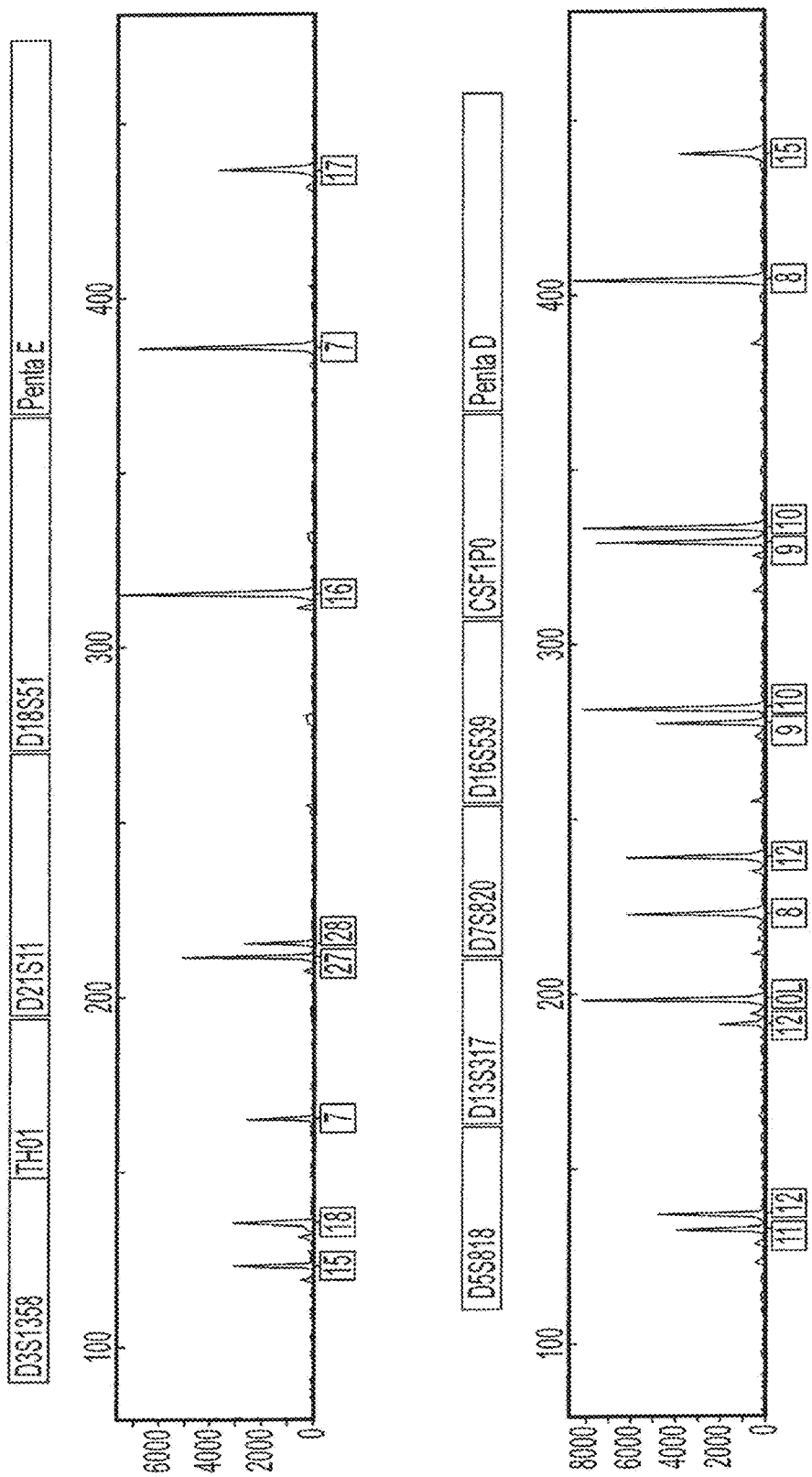
FIG. 3 presents the STR profile from the PCR amplification of unwashed HeLa cell spotted iFTAe (replicate no. 3).
Figure 3:
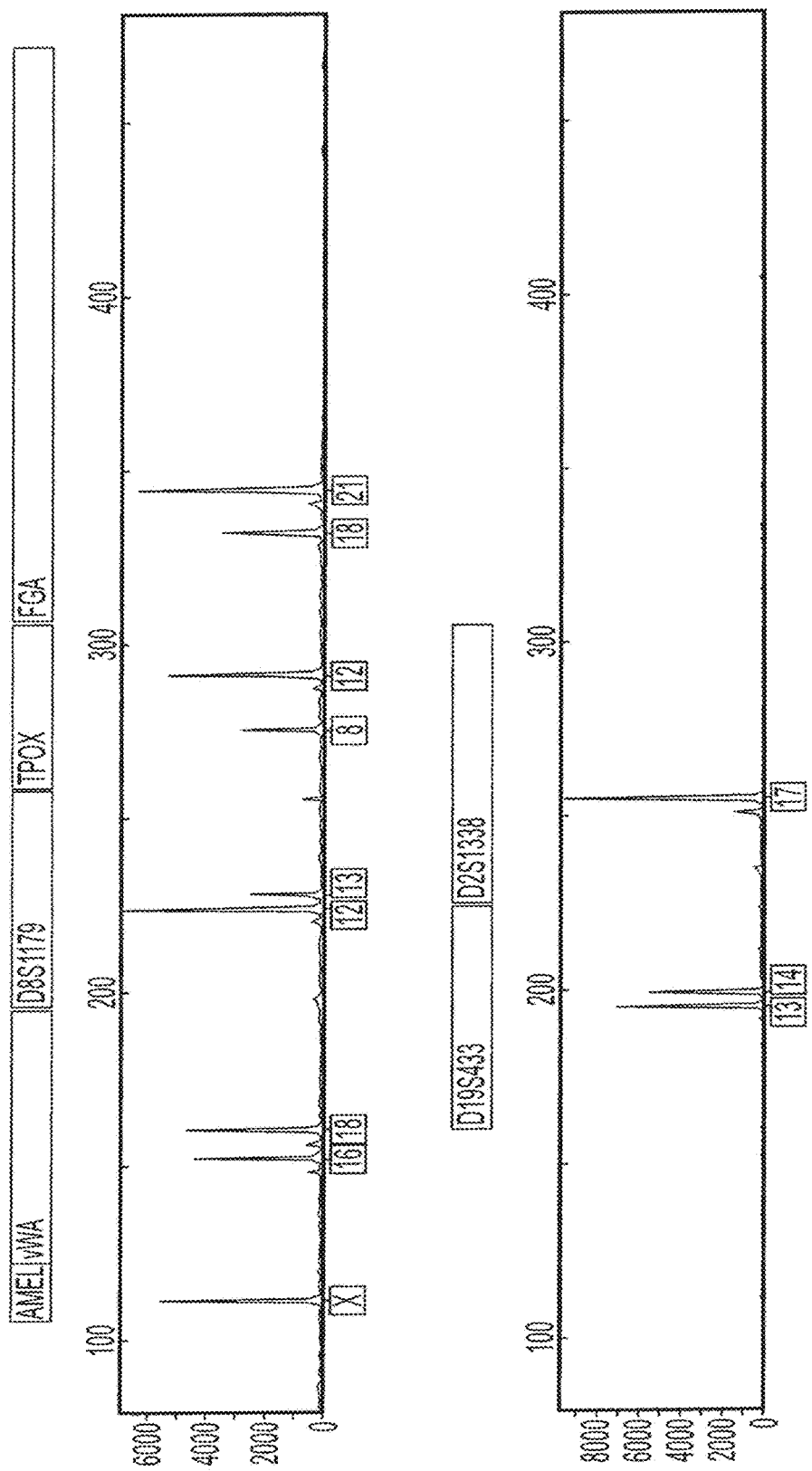

FIG. 3 shows STR profile of unwashed HeLa cell spotted indicating FTA elute card combined with STR PCR reagents (replicate 3). The average peak height was 5386 RFU.

Figure 4:
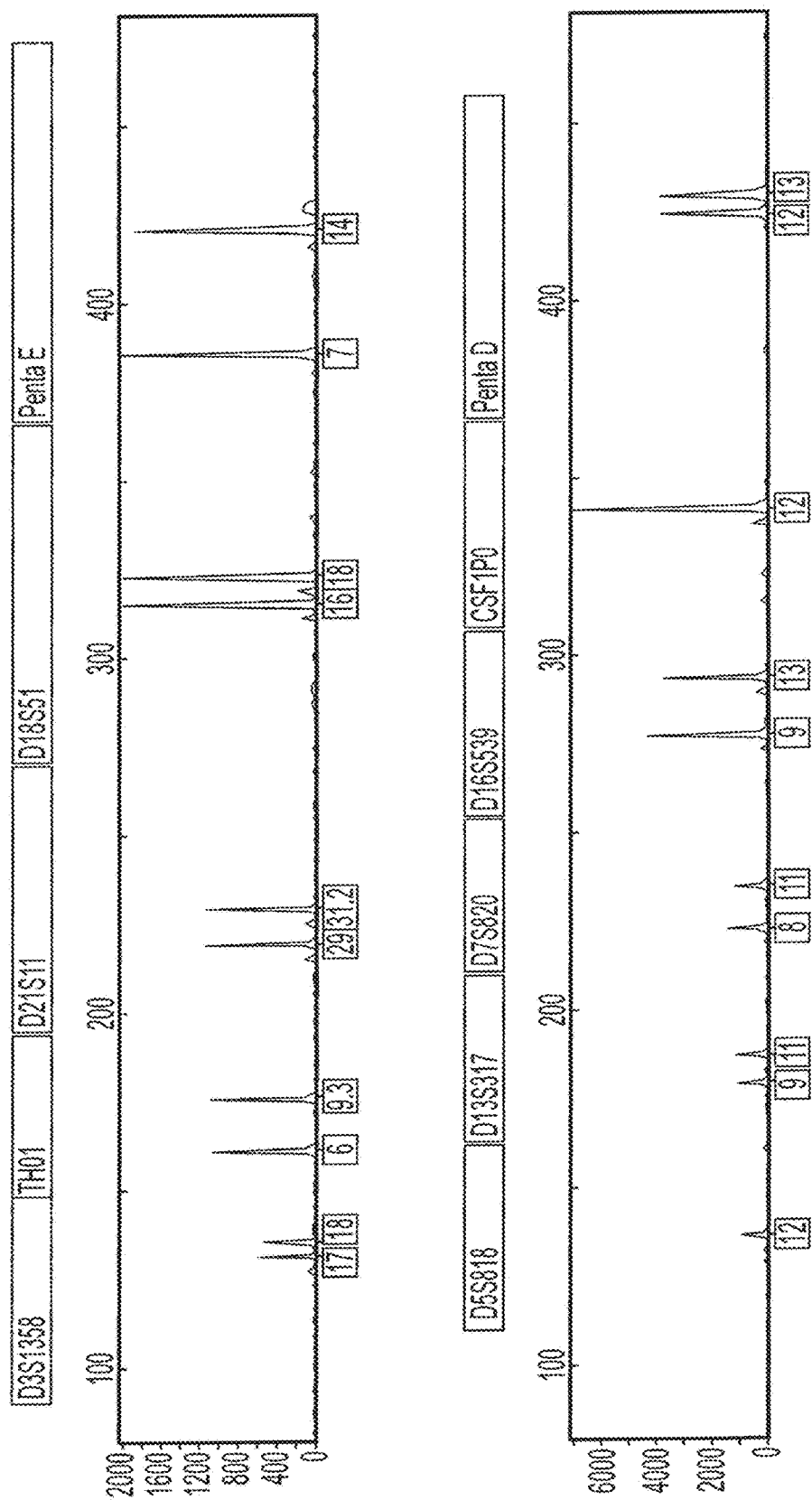
FIG. 4 presents the STR profile from the PCR amplification of control DNA sample.
Figure 4:
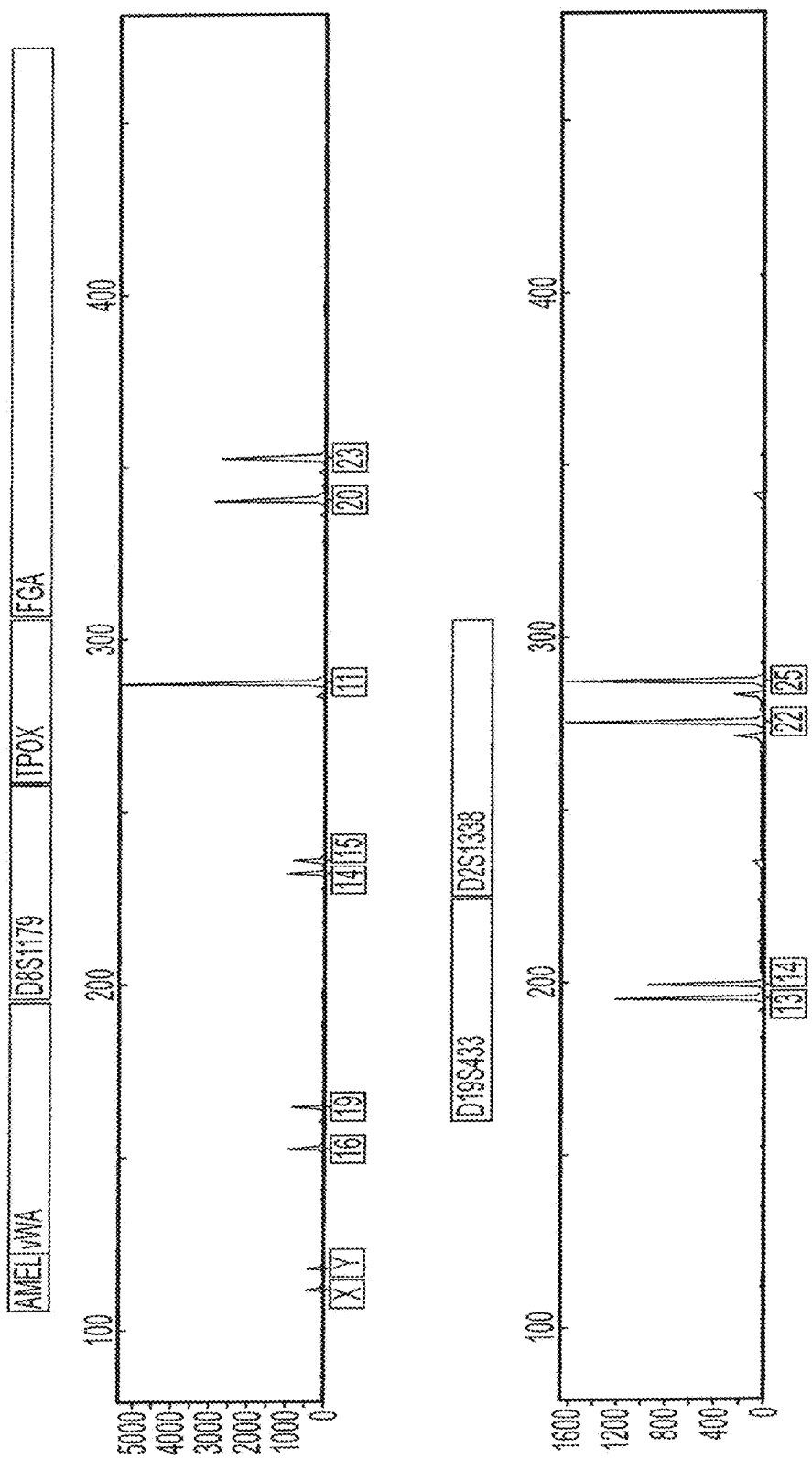

FIG. 4 shows STR profile of purified genomic DNA with STR PCR reagents. The average peak height was 1904 RFU. Quantification of DNA from HeLa Cell Spotted and Blood Spotted FTA Elute Cards Using qPCR (Table 5).

Cultured HeLa cells at a concentration of $1 \times 10^7$ cell/ml or whole blood was spotted onto an indicating FTA elute card. A 3 mm or 1.2 mm punch was taken from the cell spotted FTA elute card and eluted using the iFTAe high throughput elution protocol or washed with 1 ml of elution buffer or left unwashed. Either the sample and FTA card or 5 μl of the eluate was added to the qPCR reaction containing TaqMan Rnase P detection reagents and TaqMan Universal PCR master mix. The PCR sample mix was added to individual wells of a 96 well PCR plate prior to amplification.

Indicating FTA elute high throughput elution protocol was as follows:

3 mm punch was added into a 96 well PCR plate, 200 μl of sterile water was added to each well, the plate was sealed and pulse vortexed three times (5 seconds each). The plate was centrifuged at 1200 rpm for 2 min. The water was aspirated and discarded and 60 μl of sterile water was added to each well and the plate was sealed again. The plate was centrifuged at 1200 rpm for 2 min and placed on a thermal cycler at 98° C. for 30 min. The plate was then pulse vortexed 60 times (one pulse/sec) using a vortex mixer set on maximum speed. The plate was centrifuged at 1200 rpm for 2 mins and the eluate was removed from the wells using a pipette and transferred to another plate/well for quantification.

PCR Reaction was Set Up as Follows:

Standards and samples were added to the appropriate wells. The plates were sealed and centrifuged at 1000 rpm for 1 minute. PCR was carried out using Applied Biosystems 7900 Real-Time PCR System under the following thermal cycling conditions: 50° C. for 2 min, followed by 95° C. for 10 min, followed by 40 cycles of: 95° C. for 15 sec, 60° C. for 1 min. The detector used was the FAM™ probe. The results are presented in Table 5.

TABLE 4

Volume of reagents in the TaqMan PCR master Mix

| Ingredients | Volume |
|---|---|
| 2X Universal Master mix | 12.5 μl |
| Sterile water | 11.25 μl |
| 20X RNase P primer probe | 1.25 μl |
| 1.2 mm or 3 mm punch of FTA elute containing HeLa cells or 1.2 mm or 2 × 3 mm punch of FTA elute containing blood | 1 punch |

Table 5 shows the qPCR results of washed and unwashed blood spotted or cell spotted iFTAe card. The table shows the average yield of DNA from three qPCR reactions in ng/μl. The first 3 samples are replicates of DNA eluted from two 3 mm punches of iFTAe cards and the 4$^{th}$ sample is of a 1.2 mm punch of blood spotted iFTAe card that was washed with 1 ml of elution buffer and then amplified using real—time PCR (the data is the average of 3 separate samples). Samples 5 to 7 are replicates of DNA eluted from two 3 mm punch of an iFTAe card spotted with HeLa cells and the 8$^{th}$ sample is of a 3 mm punch HeLa spotted iFTAe card that was washed with 1 ml of elution buffer and then used in the real—time PCR machine. The last sample was of a 1.2 mm punch of HeLa spotted iFTAe card that was not washed and used directly in the real—time PCR machine (the data is the average of 3 separate samples). An unspotted negative punch did not yield any detectable DNA.

TABLE 5 qPCR results from the PCR amplification of samples of unwashed blood spotted and HeLa spotted iFTAe and pure blood samples.

| Sample | iFTAe punch size | Eluted/Direct protocol | Average yield (ng/μl) |
|---|---|---|---|
| Blood eluted from iFTAe Microcards (BATCH A) | 2 × 3 mm punch | Eluted following iFTAe protocol | 0.039 |
| Blood eluted from iFTAe Microcards (BATCH B) | 2 × 3 mm punch | Eluted following iFTAe protocol | 0.046 |
| Blood eluted from iFTAe Microcards (BATCH C) | 2 × 3 mm punch | Eluted following iFTAe protocol | 0.061 |
| Blood 1.2 mm from iFTAe Microcards | 1 × 1.2 mm punch | Direct (washed 1 ml elution buffer) | 0.039 |
| Hela cells eluted from iFTAe Microcards (BATCH A) | 1 × 3 mm punch | Eluted following iFTAe protocol | 6.025 |

TABLE 5-continued qPCR results from the PCR amplification of samples of unwashed blood spotted and HeLa spotted iFTAe and pure blood samples.

| Sample | iFTAe punch size | Eluted/Direct protocol | Average yield (ng/µL) |
|---|---|---|---|
| Hela cells eluted from iFTAe Microcards (BATCH B) | 1 × 3 mm punch | Eluted following iFTAe protocol | 5.099 |
| Hela cells eluted from iFTAe Microcards (BATCH C) | 1 × 3 mm punch | Eluted following iFTAe protocol | 5.956 |
| Hela cells 3 mm from iFTAe Microcards | 1 × 3 mm punch | Direct (washed 1 ml elution buffer) | 0.803 |
| Hela cells 1.2 mm from iFTAe Microcards | 1 × 1.2 mm punch | Direct (no wash) | 1.735 |

Figure 5:
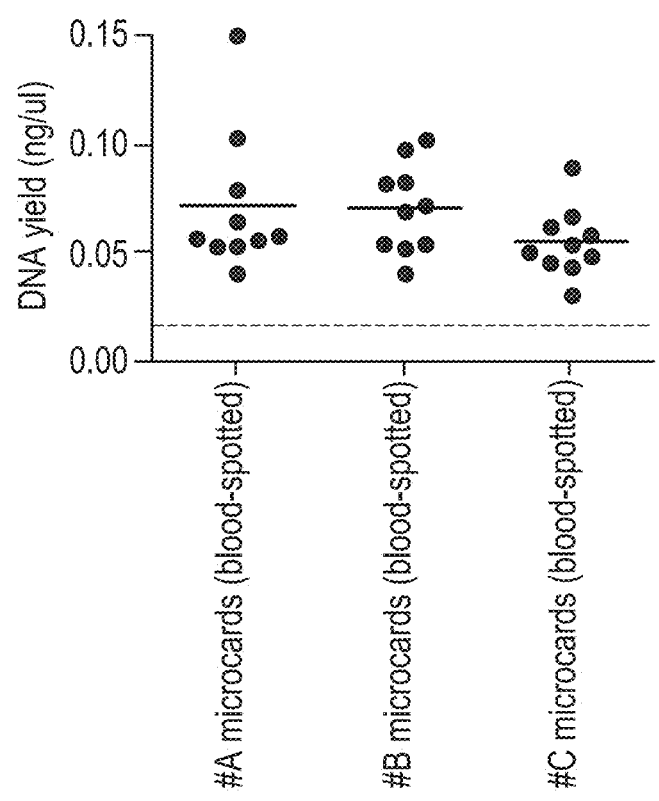
FIG. 5 presents the DNA yield from the qPCR amplification of washed blood spotted iFTAe amplified directly.
Figure 6:
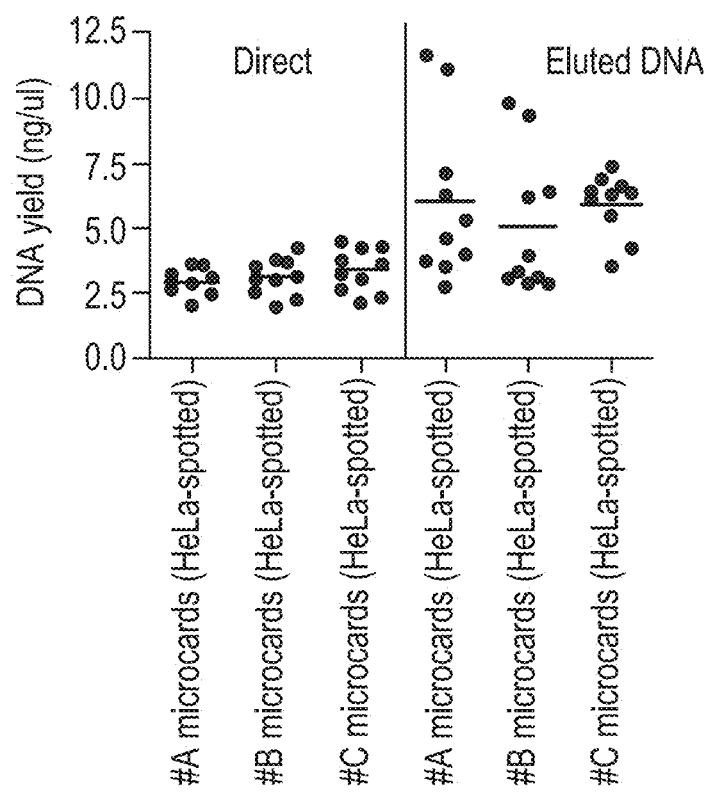
FIG. 6 presents the DNA yield from the qPCR amplification of unwashed HeLa cell spotted iFTAe either amplified directly or after being eluted.

Quantification of DNA from HeLa Cell Spotted and Blood Spotted FTA Elute Cards Using qPCR (FIGS. 5 and 6)

Cultured HeLa cells at a concentration of $7.54 \times 10^6$ cell/ml or whole blood was spotted onto an iFTAe card. A 1.2 mm (HeLa and blood samples) punch was taken from the iFTAe card and washed with 1 ml of sterile water, vortexed and water was removed or the sample was left unwashed. A 3 mm (HeLa and blood samples) punch was taken from the iFTAe card and eluted using the iFTAe high throughput elution protocol. Either the sample spotted iFTAe card or 2 or 5 µl of the eluate was added to the qPCR reaction containing TaqMan Rnase P detection reagents and TaqMan Universal PCR master mix. The PCR sample mix was added to individual wells of a 96 well PCR plate prior to amplification.

Indicating FTA elute high throughput elution protocol was as follows: For each sample to be processed 1×3 mm punch (HeLa sample) was placed into a 1.5 ml tube. 1 ml of sterile water was added to the tube and pulse vortexed three times (5 seconds each). The water was aspirated and discarded and the punches were transferred to the well of a 96 well PCR plate. 60 µl of sterile water was added to each well and the plate was sealed. The plate was centrifuged at 1200 rpm for 2 min and placed on a thermal cycler at 98° C. for 30 min. The plate was then pulse vortexed 60 times (one pulse/sec) using a vortex mixer set on maximum speed. The plate was centrifuged at 1200 rpm for 2 mins and the eluate was removed from the wells using a pipette and transferred to another plate/well for quantification. The plate was stored at 4° C. until quantification.

PCR reaction was set up as described above using Applied Biosystems 7900 Real-Time PCR System.

FIG. 5 shows DNA yield of washed blood spotted iFTAe cards used directly in a qPCR reaction. Three different batches of iFTAe cards were used in the experiment (A, B and C).

FIG. 6 shows DNA yield of unwashed HeLa cell spotted iFTAe cards either used directly in a qPCR reaction or eluated first and then used in a qPCR reaction. Three different batches of iFTAe cards were used in the experiment (A, B and C).

STR Profiles and qPCR of DNA Eluted from Blood Spotted FTA Cards Using the FTA Express Method (Table 6, 7 and 8).

DNA Elution

Four×1.2 mm punches were taken from an FTA blood spot and placed in separate tubes. Two punches were subjected to the following method with no prior punch washing:
1. Add 35 µL of Solution 1 (0.1M NaOH, 0.3 mM EDTA, pH13.0) to the punch
2. Incubate 5 minutes at room temperature
3. Add 65 µL of Solution 2 (0.1M Tris-HCl, pH7.0) and flash vortex 5 times to mix
4. Incubate 10 minutes at room temperature
5. Flash vortex 10 times
6. Remove punch and squeeze to recover maximum volume of DNA solution.

The remaining 2 punches followed the same methods but with double the amount of solution 1 and 2 above. The DNA solution was then stored at 4° C. until needed for either qPCR or STR profiling.

PowerPlex 16HS STR Profiling

STR PCR was carried out using 5 µl and 10 µl aliquots from the duplicate samples from both scales of total eluted volume (100 or 200 µl). The samples were then placed on a Geneamp 9700 Thermal cycler using the standard conditions in the instruction manual. All STR products were separated using a 3130×1 Genetic analyzer and the results analyzed using Genemapper ID software.

TABLE 6

Presents the STR profiles from the PCR amplification of DNA eluted from blood spotted FTA cards using the FTA Express method, Shown are the average peak height (relative fluorescence units) for each loci using different volumes of eluate following high pH buffer wash. 100 & 200 represent the total volume of buffer used during the wash stage.

| Loci | 100 (5 µl) | 200 (5 µl) | 100 (10 µl) | 200 (10 µl) |
|---|---|---|---|---|
| D3S1358 | 376.3 | 187.8 | 1288.0 | 586.0 |
| TH01 | 246.3 | 189.0 | 983.0 | 464.3 |
| D21S11 | 485.0 | 450.3 | 1681.8 | 951.5 |
| D18S51 | 359.0 | 217.5 | 1480.8 | 727.3 |
| Penta E | 403.8 | 325.3 | 1541.5 | 755.3 |
| D5S818 | 370.5 | 240.0 | 1192.8 | 676.3 |
| D13S317 | 469.3 | 338.3 | 1281.8 | 709.3 |
| D7S820 | 441.0 | 326.8 | 1763.5 | 852.3 |
| D16S539 | 329.0 | 259.5 | 1515.3 | 738.5 |
| CSF1PO | 152.5 | 110.5 | 684.3 | 324.8 |
| Penta D | 869.0 | 557.3 | 3596.8 | 1783.5 |
| AMEL | 342.0 | 218.3 | 1021.5 | 663.0 |
| vWA | 348.5 | 259.5 | 1155.3 | 653.5 |
| D8S1179 | 313.3 | 191.0 | 1209.5 | 532.8 |
| TPOX | 221.8 | 156.3 | 859.3 | 410.0 |
| FGA | 607.8 | 521.0 | 1450.8 | 1084.5 |
| Overall | 395.9 | 284.2 | 1419.1 | 744.5 |

Criteria for Acceptance

Pass criteria—STR allelic peaks are expected to be higher than 75 RFU's for heterozygote peaks and higher than 150 RFU's for homozygote peaks. Negative controls are expected to produce no profiles, i.e. no peaks on ladder above 50 RFU's. Positive controls are expected to be higher than 75 RFU's for heterozygote peaks and higher than 150 RFU's for homozygote peaks.

TABLE 7

The total number of alleles present after STR profiling using different volumes of eluate following high pH elution and neutralisation. The total number of alleles that were possible to obtain was noted only if a partial profile (PP) was obtained. A & B are represented as replicate, 100 & 200 represent the volume of the total buffer used.

| | 100 A | 100 B | 200 A | 200 B |
|---|---|---|---|---|
| 5 µl | FP | PP 30/32 | PP 31/32 | FP |
| 10 µl | FP | FP | FP | FP |

Quantifiler qPCR

All qPCR was carried out on a 7900HT Real time PCR machine and analyzed using SDS 2.3 software.

The standard reaction mix volumes and instruments protocols were used as described in the Quantifiler user guide. Four replicates of each elution volume were tested.

All standards for the qPCR assay passed as expected, with all samples for both elution volumes also returning quantification values, as summarized in Table 8 below.

TABLE 8

Average yields returned for each elution volume used to extract DNA from blood spotted FTA cards. Both elution volumes returned an average yield close to 0.12 ng/µl.

| Elution Volume | Mean Quantity (ng/µl) | Quantity Standard Deviation | Mean Ct Value |
|---|---|---|---|
| 100 µl | 0.121 | 0.0126 | 31.88 |
| 200 µl | 0.116 | 0.0214 | 31.95 |

Both the qPCR and STR profiling assays provided results suggesting that the FTA Express high pH method is comparable to that described in the standard published Whatman application note (Eluting Genomic DNA from FTA® Cards Using Room Temperature pH Treatment) and all other known protocols that state the need for extensive washing for removal of inhibitory chemistry prior to high pH elution. By removing wash procedures, the chance of losing small punches performed by combined automated punch and wash systems is eliminated leading improved throughput and reduced costs.

Use of FTA Express Methodology with Aged Museum Sample of Preserved Fish Tissue.

A sample of Mackerel (Somber Sumbrus) preserved in 100% ethanol since 2003 was homogenised in phosphate buffered saline (PBS) with a Qiagen Tissue Ruptor Probe using approximately 5 mm³ tissue per 180 µl PBS. Aliquots of 10 µl were pipetted onto FTA cards and dried overnight. To evaluate the effectiveness of minimal washing prior to high pH elution of sample DNA from punched FTA discs, triplicate discs were obtained and processed according to the following:
1. Standard wash according to standard Whatman method of punch washing;
2. A single wash using $TE^{-1}$ buffer;
3. No washes but with the addition of alpha-cyclodextrin to a final concentration of 2% (w/v) in the PCR;
4. No washes at all prior to high pH elution.

The processed triplicate punches were then expose to the following elution protocol:
Solution 1: 0.1N NaOH, 0.3 mM EDTA, pH13.0
Solution 2: 0.1M TrisHCl, pH7.0
Time Scheme: High pH for 10 min, neutralized for 5 min 1. Add 20 µl of Solution 1 to a 3 mm punch (washed by normal protocol)
2. Incubate 10 minutes on ice
3. Add 40 µl of Solution 2 and flash vortex 5 times to mix
4. Incubate 5 minutes at room temperature, Flash vortex 10 times.

The 3 mm punches in a total volume of 60 µl were then sampled to triplicate tubes with 3 µl DNA solution added to the assembled PCR (final 25 µl volume) from each of the differentially processed samples. Three different primer pairs were used in independent amplification reactions: Sscox1-1/Sscox1-2 (expected 138 bp product size); Sscox1-1/Sscox1-3 (expected 265 bp product size); Sscox1-1/Sscox1-4 (expected 451 bp product size). Note also that positive and negative control amplification samples were also ran on an analytical 1% agarose gel containing a DNA interchelating dye. What was shown was that the negative controls were negative, however with the optimised workflow of eluting DNA at high pH without preparative washes proved equally successful with aged and preserved tissue samples (FIG. 7).

Figure 7:
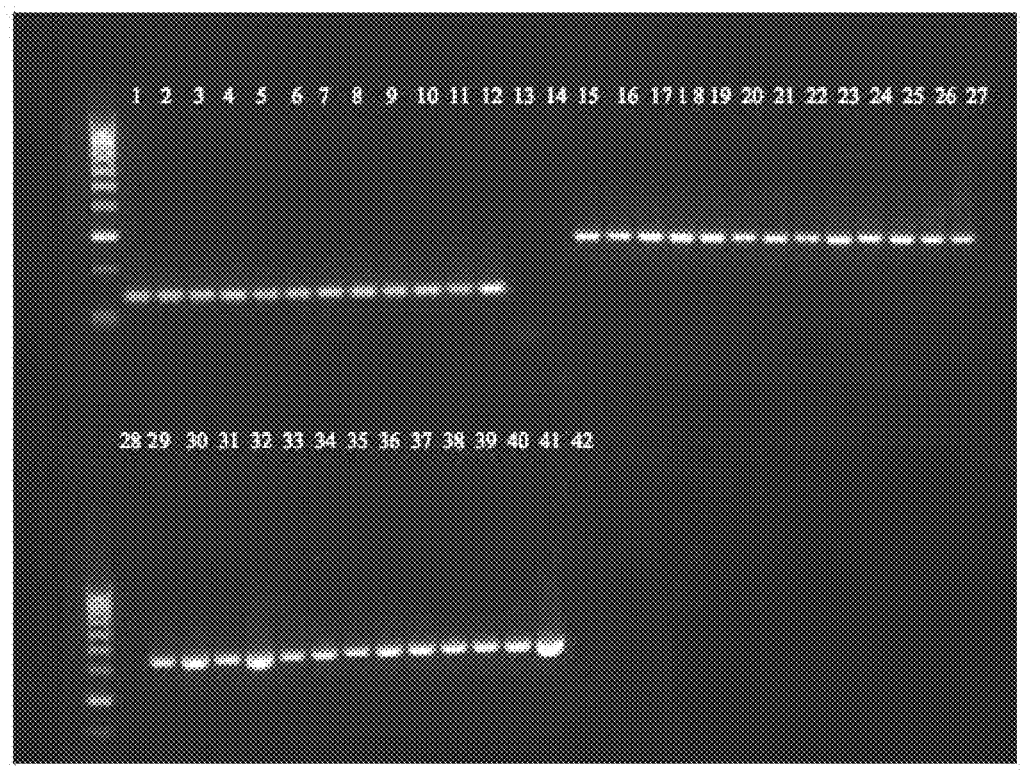
FIG. 7 presents the amplification of DNA targets from homogenised museum samples applied to ambient storage FTA cards using optimised FTA Express methodology.

FIG. 7 shows results of amplification of DNA targets from homogenised museum samples applied to ambient storage FTA cards using optimised FTA Express methodology. The agarose gel of amplified samples shows that the approach of eluting DNA from FTA punches in the absence of any removal of impregnated chemistry by exhaustive washing provides DNA solutions suitable for successful PCR (lanes 1-3, 15-17 and 29-31: standard wash; lanes 4-6, 18-20 and 32-34: single wash; lane 7: No washes+2% Neutralizer, Sscox1-1/1-2 All; lane 21: No washes+2% Neutralizer, Sscox1-1/1-3 All; lane 35: No washes+2% Neutralizer, Sscox1-1/1-4 All; lane 8: No washes+2% Neutralizer products 138 bp; lane 22: No washes+2% Neutralizer products 265 bp; lane 36: No washes+2% Neutralizer products 451 bp; lanes 9, 23 and 37: No washes+2% Neutralizer; lanes 10-12, 24-26 and 38-40: no wash; lanes 14, 28 and 42: negative control; lanes 27 and 41: positive control).

Validation of the FTA Express Method for miRNA Detection from FTA Cards:

Certain RNA species like miRNA are naturally small (~22 nucleotides) and are therefore easily lost during conventional extraction and purification steps. One of skill in the art would also appreciate that alkaline pH solutions catalyze 2'-hydroxyl trans-esterification reactions in RNA, but not DNA, and may exacerbate RNA degradation and loss. To evaluate the compatibility of the FTA Express method with RNA species, FTA cards were spotted with synthetic miRNAs and analyzed by RT-PCR using the FTA Express method as follows:

Materials:
1) Whatman Indicating FTA Classic Card (GE Healthcare, cat#WB120206, lot#FT6902011)
2) miR21-5p (5'-UAGCUUAUCAGACUGAUGUUGA-3' (SEQ ID NO. 1), synthesized by IDT)
3) Let7i-5p (5'-UGAGGUAGUAGUUUGUGCUGUU-3' (SEQ ID NO. 2), synthesized by IDT)
4) Solution 1 (0.1M NaOH, 0.3 mM EDTA, pH13.0)
5) Solution 2 (0.1 mM Tris-HCl, pH7.0)
6) miScript RT Kit (Qiagen, cat#218161)
7) miScript Primer Assay (Qiagen, Hs_miR21_2, cat#MS00009079) Lot#118346858)
8) miScript primer Assay (Qiagen, Hs_Let7i_1, cat#MS00003157) lot#168331862)
9) miScript SYBR Green PCR Kit (Qiagen, cat#218073)
10) α-Cyclodextrin (sigma, cat# C4680-1G), make 8% (w/v) in nuclease free water 11) PCR plate (ABI, MicroAMP Fast Optical 96-well Reaction plate with Barcode, ref#4346906)

Sample Preparation:

Punches of FTA Classic were prepared using a 1.2 mm UniCore puncher and 210 ng of synthetic miRNAs (either miR21-5p or Let7i-5p) were spotted onto each punch in 1 µl aliquots. Samples were dried at room temperature overnight.

Sample Extraction by FTA Express Method:

Each 1.2 mm punch was resuspended in 35 µL of Solution 1 (0.1M NaOH, 0.3 mM EDTA, pH 13.0), incubated for 5 minutes at room temperature, and neutralized with 65 µL of Solution 2 (0.1 mM Tris-HCl, pH 7.0) using a flash vortex to mix. Samples were further incubated for 5 minutes at room temperature, flash vortexed to mix, and the punch was removed from solution and pressed to recover a maximum volume of RNA solution (~100 µl).

Reverse Transcription (RT):

RT reaction mixtures were prepared using the miScript RT kit (Qiagen, cat#218161). Briefly, 4 µl of 5×miScript HiSpec Buffer, 2 µl of 10× miScript Nucleics Mix, 2 µl of miScript RT Mix, 4 µl of 8% α-cyclodextrin (w/v), 6 µl nuclease-free water, and 2 µl of FTA Express eluate (~2% of total volume extracted above) were combined in a 0.2 ml tube. Control reactions were prepared in parallel using synthetic miRNAs at equivalent input. Reactions were incubated at 37° C. for 1 hour, followed by 5 minutes at 95° C. to inactivate enzymes.

cDNA Template Preparation:

A 1:10 dilution of cDNA was prepared by adding 180 µl of nuclease-free water to each of the 20 µl RT reactions described above. This cDNA stock was serially diluted to 1:100 and 1:400 in nuclease-free water.

Quantitative PCR Detection (qPCR):

qPCR reactions were prepared using the miScript SYBR Green PCR kit (Qiagen, cat#218073). Briefly, 12.5 µl of 2×SYBR Green PCR Master mix, 2.5 µl of 10× miScript Universal Primer, 5.5 µl of nuclease-free water, and 2.5 µl of 10× miScript Primer (Hs_miR21_2, cat#MS00009079 or Hs_Let7i_1, cat#MS00003157) were combined as a master mix. Diluted cDNA template (1:100 and 1:400 stocks) was added in 2 µl aliquots into a 96-well PCR plate and subsequently mixed with 23 µl of master mix per well. Each sample and dilution was prepared in this manner in triplicate, and qPCR reactions were incubated in a 7500 Fast Real-Time PCR instrument according to the following parameters: 95° C./15 min, (95° C./15 sec, 55° C./30 sec, 70° C./30 sec)×40 cycles.

The Results set forth in TABLE 9 demonstrate robust and quantitative detection of synthetic miRNAs from FTA punches using the FTA Express method. Relative to solution control reactions, these qPCR results suggest ~50% functional recovery of miRNA from FTA punches using the FTA Express method.

TABLE 9

Synthetic miRNA comparison (FTA Express vs. Solution Control)

| Template | cDNA dilution | Solution $C_T$ | FTA Express $C_T$ |
|---|---|---|---|
| Synthetic miR21 | 1:100 | 6.3 | 11.2 |
|  | 1:400 | 7.9 | 13.2 |
| Synthetic Let7i | 1:100 | 5.9 | 12.3 |
|  | 1:400 | 7.4 | 13.9 |
| No RT control | 1:100 | 34.9 | 34.2 |
|  | 1:400 | 34.6 | 33.9 |

To extend this capability to physiological RNA, we repeated these experiments with total RNA purified from MCF-7 cells (Life Technologies, cat#AM7846), a breast adenocarcinoma cell line that is understood to express elevated levels of miR21. FTA cards spotted with MCF-7 total RNA were analyzed using the FTA Express method as follows:

Materials:
1) Whatman Indicating FTA Classic Card (GE Healthcare, cat#WB120206, lot#FT6902011)
2) MCF-7 total RNA (Life Technologies, cat#AM7846)
3) Solution 1 (0.1M NaOH, 0.3 mM EDTA, pH13.0)
4) Solution 2 (0.1 mM Tris-HCl, pH7.0)
5) miScript RT Kit (Qiagen, cat#218161)
6) miScript Primer Assay (Qiagen, Hs_miR21_2, cat#MS00009079) Lot#118346858)
7) miScript primer Assay (Qiagen, Hs_Let7i_1, cat#MS00003157) lot#168331862)
8) miScript SYBR Green PCR Kit (Qiagen, cat#218073)
9) α-Cyclodextrin (sigma, cat# C4680-1G), make 8% (w/v) in nuclease free water
10) PCR plate (ABI, MicroAMP Fast Optical 96-well Reaction plate with Barcode, ref#4346906)

Sample Preparation:

Punches of FTA Classic were prepared using a 1.2 mm UniCore puncher and 1 µl of 1 mg/ml total RNA (1 µg) from MCF-7 cells was spotted onto each punch in 1 µl aliquots. Samples were dried at room temperature overnight.

Sample Extraction by FTA Express Method:

Each 1.2 mm punch was resuspended in 35 µL of Solution 1 (0.1M NaOH, 0.3 mM EDTA, pH 13.0), incubated for 5 minutes at room temperature, and neutralized with 65 µL of Solution 2 (0.1 mM Tris-HCl, pH 7.0) using a flash vortex to mix. Samples were further incubated for 5 minutes at room temperature, flash vortexed to mix, and the punch was removed from solution and pressed to recover a maximum volume of RNA solution (~100 µl).

Reverse Transcription (RT):

RT reaction mixtures were prepared using the miScript RT kit (Qiagen, cat#218161). Briefly, 4 µl of 5× miScript HiSpec Buffer, 2 µl of 10× miScript Nucleics Mix, 2 µl of miScript RT Mix, 4 µl of 8% α-cyclodextrin (w/v), 6 µl nuclease-free water, and 2 µl of FTA Express eluate (~2% of total volume extracted above) were combined in a 0.2 ml tube. Reactions were incubated at 37° C. for 1 hour, followed by 5 minutes at 95° C. to inactivate enzymes.

cDNA Template Preparation:

A 1:10 dilution of cDNA was prepared by adding 180 µl of nuclease-free water to each of the 20 µl RT reactions described above. This cDNA stock was serially diluted to 1:100 and 1:400 in nuclease-free water.

Quantitative PCR Detection (qPCR):

qPCR reactions were prepared using the miScript SYBR Green PCR kit (Qiagen, cat#218073). Briefly, 12.5 µl of 2×SYBR Green PCR Master mix, 2.5 µl of 10× miScript Universal Primer, 5.5 µl of nuclease-free water, and 2.5 µl of 10× miScript Primer (Hs_miR21_2, cat#MS00009079 or Hs_Let7i_1, cat#MS00003157) were combined as a master mix. Diluted cDNA template (1:10, 1:100, and 1:400 stocks) was added in 2 µl aliquots into a 96-well PCR plate and subsequently mixed with 23 µl of master mix per well. Each sample and dilution was prepared in this manner in triplicate, and qPCR reactions were incubated in a 7500 Fast Real-Time PCR instrument according to the following parameters: 95° C./15 min, (95° C./15 sec, 55° C./30 sec, 70° C./30 sec)×40 cycles.

The Results set forth in TABLE 10 demonstrate robust and comparative detection of physiological miRNAs from FTA punches using the FTA Express method. Proportionally higher CT values are detected for mir21 at all tested cDNA dilutions relative to Let7i, consistent with the known overexpression of mir21 in MCF-7 breast adenocarcinoma cells. Thus, the FTA Express method is suitable for comparative RNA expression analysis.

TABLE 10

Physiological miRNA comparison from total RNA (FTA Express method)

| Total RNA (MCF-7 cells) | cDNA dilution | miR21 $C_T$ | Let7i $C_T$ | No RT $C_T$ |
|---|---|---|---|---|
| FTA punch | 1:10 | 19.1 | 26.0 | 32.6 |
| | 1:100 | 22.9 | 29.2 | 34.2 |
| | 1:400 | 24.0 | 30.7 | 33.9 |

All patents, patent publications, and other published references mentioned herein are hereby incorporated by reference in their entireties as if each had been individually and specifically incorporated by reference herein. While preferred illustrative embodiments of the present invention are described, one skilled in the art will appreciate that the present invention can be practiced by other than the described embodiments, which are presented for purposes of illustration only and not by way of limitation. The present invention is limited only by the claims that follow.

What is claimed is:

1. A method for amplification of nucleic acid comprising the steps:
   i) transferring, to a reaction vessel, a solid support comprising an impregnated chemistry contacted with a cellular sample containing a target nucleic acid;
   ii) incubating said nucleic acid on the solid support with a high pH solution sufficient to elute the nucleic acid from said sample, wherein the high pH solution has a pH between 12 and 13;
   iii) amplifying the nucleic acid to produce amplified nucleic acid; and
   iv) quantifying the amplified nucleic acid,
   wherein steps i) to iv) are carried out in the presence of the solid support.

2. The method of claim 1, wherein the eluted nucleic acid is contained in a minimum volume of five microliters.

3. The method of claim 1, wherein the method of elution further comprises the addition of a neutralizing solution prior to the amplifying step.

4. The method of claim 1, wherein the method of amplification comprises reverse transcription polymerase chain reaction, isothermal amplification or quantitative polymerase chain reaction.

5. The method of claim 3, wherein the eluted nucleic acid comprises a DNA or RNA species.

6. The method of claim 5, wherein said nucleic acid is amplified in the presence of an RNase inhibitor and alpha-cyclodextrin such that amplification occurs efficiently and without loss or inhibition.

7. The method of claim 1, wherein the nucleic acid amplification reagent solution comprises a polymerase, deoxyribonucleotide triphosphate (dNTP), a reaction buffer and at least one primer, wherein said primer is optionally labelled with a dye.

8. The method of claim 1, wherein the composition of the solid support comprises at least one of guanidine thiocyanate, guanidine chloride, guanidine hydrochloride, sodium dodecyl sulphate, uric acid, EDTA, and Tris buffer.

9. The method of claim 1, wherein the solid support is washed with an aqueous solution prior to step i).

10. The method of claim 1, wherein the solid support is selected from the group consisting of a glass or silica-based solid phase medium, a plastics based solid phase medium, a cellulose-based solid phase medium, glass fiber, glass microfiber, silica, gel, silica oxide, nitrocellulose, carboxymethylcellulose, polyester, polyamide, carbohydrate polymers, polypropylene, polytetraflurorethylene, polyvinylidinefluoride, wool and porous ceramics.

11. The method of claim 1, wherein the solid support is a cellulose based matrix.

12. The method of claim 11, wherein said cellulose based matrix is in the form of a pre punched disc.

13. The method of claim 1, wherein the nucleic acid is DNA and the method further comprises
   v) using Short Tandem Repeat (STR) profiling to produce an STR profile.

14. The method of claim 1, wherein the nucleic acid is mRNA, miRNA, rRNA, piRNA, or siRNA and the method further comprises gene expression analysis.

15. A method for amplification of nucleic acid comprising the steps:
   i) contacting a solid support comprising a chaotropic salt with a cellular sample containing nucleic acid;
   ii) transferring said solid support to a reaction vessel;
   iii) incubating said nucleic acid on the solid support with a high pH solution sufficient to elute the nucleic acid from said sample, wherein the high pH solution has a pH between 12 and 13;
   iv) incubating said nucleic acid with a nucleic acid amplification reagent solution;
   v) amplifying the nucleic acid to produce amplified nucleic acid;
   vi) quantifying the amplified nucleic acid; and
   vii optionally, using Short Tandem Repeat (STR) profiling to produce an STR profile,
   wherein steps i) to vii) are carried out in the presence of the solid support.

16. A method for amplification of nucleic acid comprising the steps:
   i) contacting a solid support comprising a lysis reagent with a cellular sample containing nucleic acid;
   ii) transferring said solid support to a reaction vessel;
   iii) incubating said nucleic acid on the solid support with a high pH solution sufficient to elute the nucleic acid from said sample, wherein the high pH solution has a pH between 12 and 13;
   iv) incubating said nucleic acid with a nucleic acid amplification reagent solution;
   v) amplifying the nucleic acid to produce amplified nucleic acid; and
   vi) optionally, quantifying the amplified nucleic acid;
   wherein steps i) to vi) are carried out in the presence of the solid support.

* * * * *